United States Patent
Bond et al.

(10) Patent No.: US 7,363,817 B2
(45) Date of Patent: *Apr. 29, 2008

(54) SYSTEM AND TECHNIQUE FOR DETECTING THE PRESENCE OF FOREIGN MATERIAL

(75) Inventors: Leonard J. Bond, Richland, WA (US); Aaron A. Diaz, Richland, WA (US); Richard A. Pappas, Richland, WA (US); Timothy L. Stewart, Pendleton, OR (US); Albert Mendoza, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 461 days.

This patent is subject to a terminal disclaimer.

(21) Appl. No.: 10/496,744

(22) PCT Filed: Nov. 27, 2002

(86) PCT No.: PCT/US02/38006

§ 371 (c)(1),
(2), (4) Date: Oct. 12, 2004

(87) PCT Pub. No.: WO03/046548

PCT Pub. Date: Jun. 5, 2003

(65) Prior Publication Data

US 2005/0068535 A1    Mar. 31, 2005

Related U.S. Application Data

(63) Continuation-in-part of application No. 10/228,976, filed on Aug. 27, 2002, now Pat. No. 6,992,771, which is a continuation-in-part of application No. 10/000,263, filed on Nov. 28, 2001, now Pat. No. 6,786,096.

(51) Int. Cl.
*G01N 29/04* (2006.01)
*G01N 21/55* (2006.01)

(52) U.S. Cl. .................. 73/598; 73/602; 356/445; 250/223 R

(58) Field of Classification Search ............ None
See application file for complete search history.

(56) References Cited

U.S. PATENT DOCUMENTS 2,966,056 A    12/1960    Heller ............ 73/67.76

(Continued)

FOREIGN PATENT DOCUMENTS

EP    0 352 078 A3    1/1990    ............ 21/89

(Continued)

OTHER PUBLICATIONS

PCT/US02/38006 International Preliminary Examination Report dated Apr. 18, 2006.

(Continued)

*Primary Examiner*—Michael A. Lyons
*Assistant Examiner*—Juan D Valentin, II
(74) *Attorney, Agent, or Firm*—Woodard Emhardt Moriarty McNett & Henry LLP

(57) ABSTRACT

Systems and techniques for detecting the presence of foreign material in food utilizing optical backlighting and/or ultrasonic inspection are presented. In optical backlighting, a substantially monochromatic light source optically backlights a food stream with source light having a wavelength between about 500 and 600 nm. An image of the food stream is captured and the presence of foreign material is determined when a portion of the detected image exceeds a predetermined threshold. The technique is especially suitable for the detection of bone in chicken meat, and the light source can be a planar array of green LEDs. In ultrasonic inspection, a process stream is interrogated with pulses of ultrasound and the presence of foreign material is determined based on the detected off-angle ultrasound scattering response.

12 Claims, 21 Drawing Sheets

U.S. PATENT DOCUMENTS

| | | | |
|---|---|---|---|
| 4,208,915 A | 6/1980 | Edwards | 73/620 |
| 4,214,484 A | 7/1980 | Abts | |
| 4,217,781 A | 8/1980 | Abts | |
| 4,226,540 A | 10/1980 | Barten et al. | 356/445 |
| 4,339,944 A | 7/1982 | Abts et al. | |
| 4,384,476 A | 5/1983 | Black et al. | 73/61 |
| 4,527,420 A | 7/1985 | Foote | 73/61 |
| 4,542,644 A | 9/1985 | Claytor et al. | 73/61 |
| 4,631,413 A | 12/1986 | Jensen et al. | 250/458.1 |
| 4,735,097 A | 4/1988 | Lynnworth | 73/861.28 |
| 4,821,573 A | 4/1989 | Nagata et al. | 73/597 |
| 4,829,184 A | 5/1989 | Nelson et al. | 250/358.1 |
| 4,894,201 A | 1/1990 | Ahmed | 376/261 |
| 4,978,225 A | 12/1990 | Reimer | 356/432 |
| 5,059,031 A | 10/1991 | Hamel et al. | 356/428 |
| 5,062,299 A | 11/1991 | Davis et al. | 73/609 |
| 5,213,830 A | 5/1993 | Haagensen et al. | 426/237 |
| 5,241,365 A | 8/1993 | Haagensen | 356/376 |
| 5,291,773 A | 3/1994 | Kamon | 73/24.03 |
| 5,351,560 A | 10/1994 | Russwurm | 73/861.27 |
| 5,504,572 A | 4/1996 | Taylor et al. | 356/53 |
| 5,528,359 A | 6/1996 | Taguchi | 356/237.6 |
| 5,641,907 A | 6/1997 | Haagensen | 73/620 |
| 5,684,252 A | 11/1997 | Kessler et al. | 73/618 |
| 5,723,773 A | 3/1998 | Bryan | 73/61.75 |
| 5,745,228 A | 4/1998 | Hebrank et al. | 356/53 |
| 5,847,382 A | 12/1998 | Koch et al. | 250/223 |
| 5,981,892 A | 11/1999 | Baird et al. | 209/590 |
| 6,061,086 A | 5/2000 | Reimer et al. | 348/125 |
| 6,167,759 B1 | 1/2001 | Bond et al. | 73/602 |
| 6,176,132 B1 | 1/2001 | MacLauchlan | 73/290 |
| 6,324,901 B1 | 12/2001 | Fluh et al. | |
| 6,401,538 B1 | 6/2002 | Han et al. | 73/599 |
| 6,532,064 B1 | 3/2003 | Hearn et al. | |
| 6,646,218 B1 | 11/2003 | Campbell et al. | |
| 6,786,096 B2 | 9/2004 | Bond et al. | 73/598 |

FOREIGN PATENT DOCUMENTS

| | | | | |
|---|---|---|---|---|
| EP | 0 361 625 A3 | 4/1990 | | 33/12 |
| EP | 1 092 976 A2 | 9/2000 | | 29/2 |
| GB | 1202861 | 8/1970 | | 21/2 |
| JP | 4 166063 | 6/1992 | | |
| WO | WO 90/04782 | 5/1990 | | 33/12 |
| WO | WO 94/03793 | 2/1994 | | 33/2 |
| WO | WO 95/21375 | 8/1995 | | 21/27 |

OTHER PUBLICATIONS

Goebbels, K., "Structure Analysis by Scattered Ultrasonic Radiation", Research Technology in NDT, vol. 4, Chapter 4, Shafe. Academic Press.

Proceedings of the 16th International Congress on Acoustics and the 135th Meeting of the Acoustical Society of American, Jun. 20-26, 1998, Seattle, WA.

Bond, L.J. and Saffari, N, "Mode-conversion Ultrasonic Testing", Chapter 5; Nondestructive Testing, vol. 7, pp. 146-189, ISBN 0-12-639057-6, 1984, Academic Press, London.

Lawrie, W.E., "Ultrasonic Nondestructive Coating Evaluation", AF Conference Proceedings, pp. 343-371 (1964).

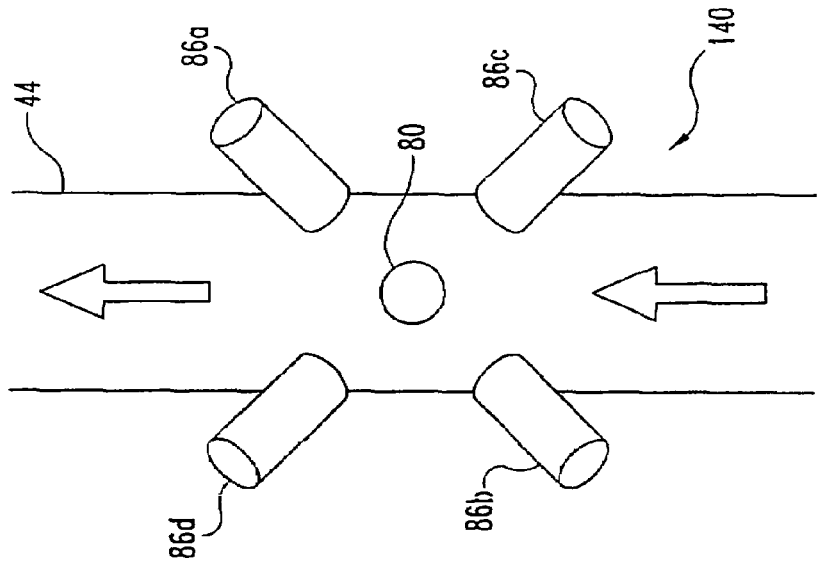
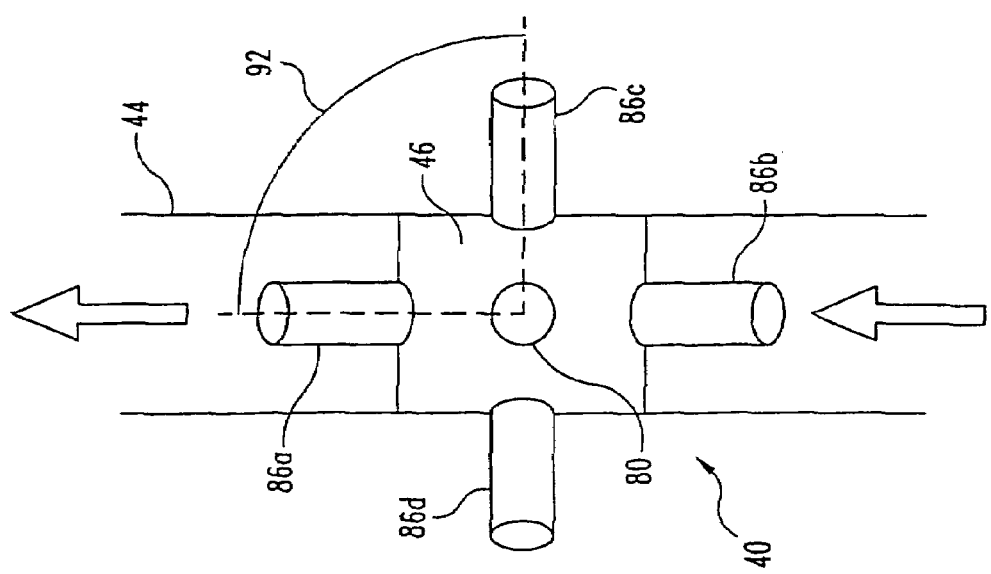

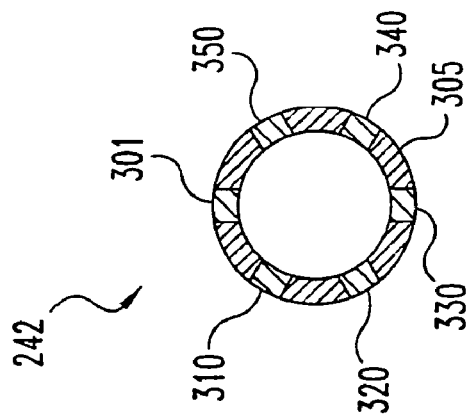
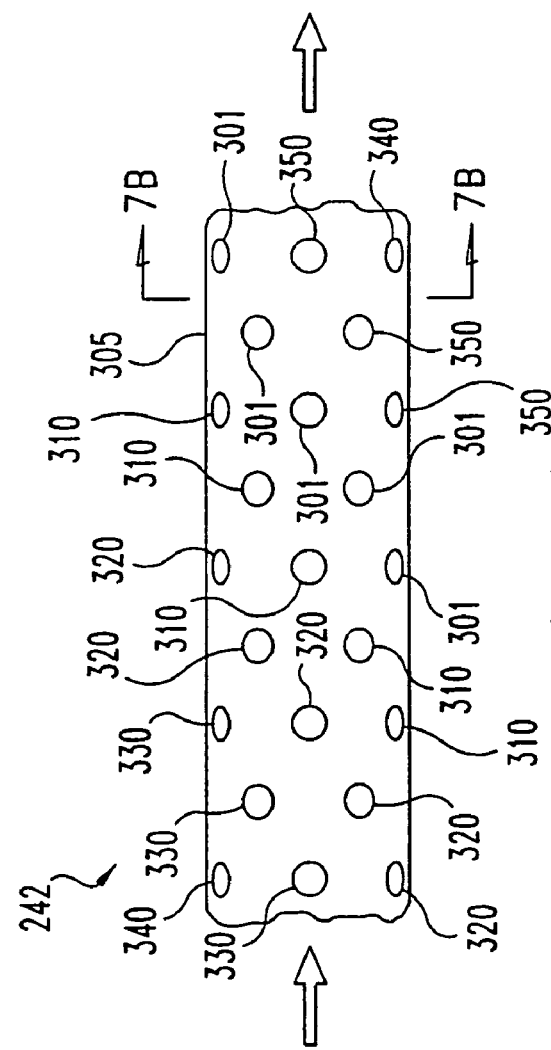

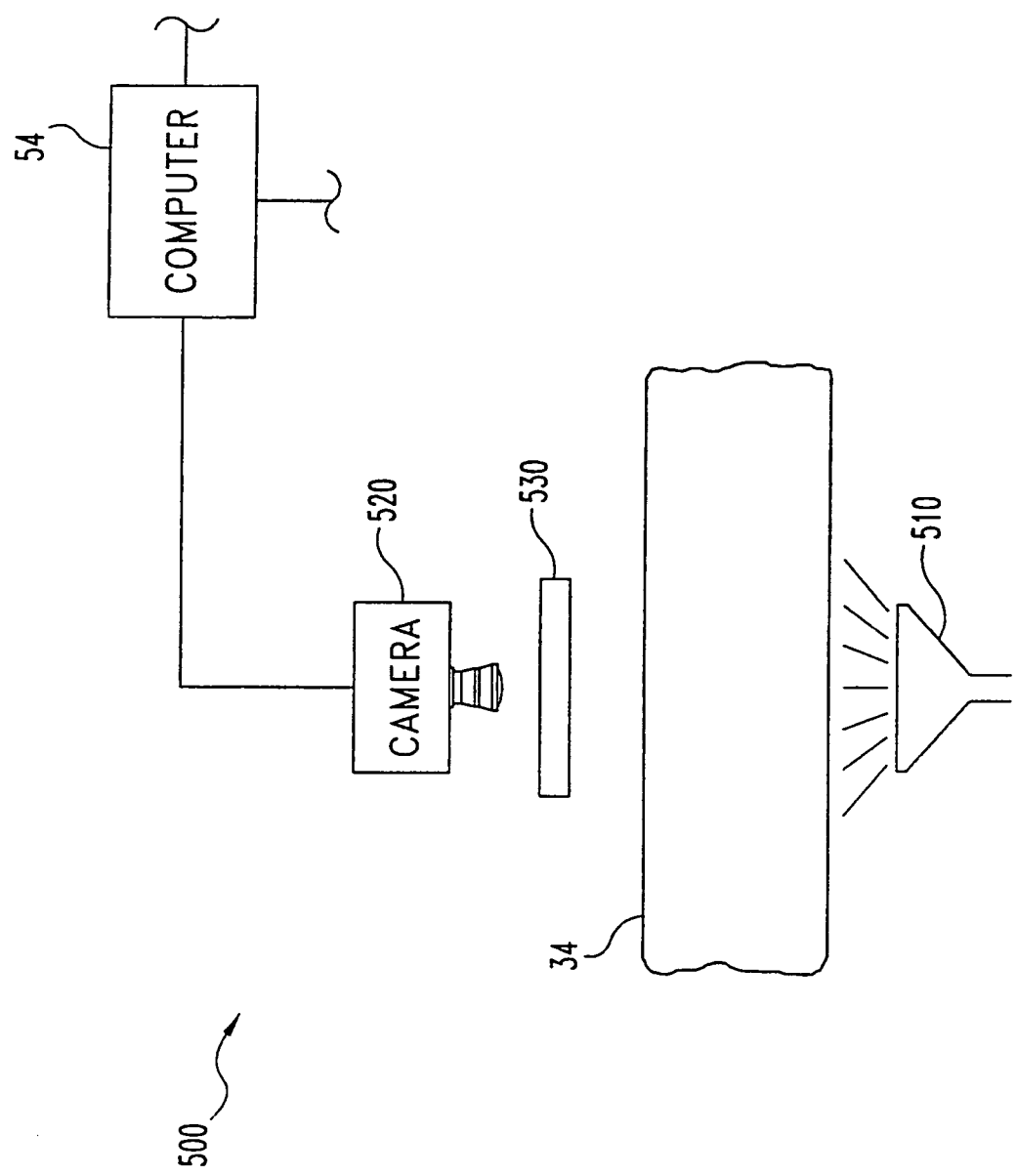

SYSTEM AND TECHNIQUE FOR DETECTING THE PRESENCE OF FOREIGN MATERIAL

RELATED APPLICATION DATA

The present application is a continuation-in-part of U.S. application Ser. No. 10/228,976, filed Aug. 27, 2002, now U.S. Pat. No. 6,992,771, which is a continuation-in-part of U.S. application Ser. No. 10/000,263 filed Nov. 28, 2001, now U,S. Pat. No. 6,786,096, the disclosures of which are hereby incorporated by reference.

BACKGROUND

The present invention is directed to the detection of foreign material. More particularly, but not exclusively, it is directed to the detection of foreign material in heterogeneous process streams such as process streams of foodstuffs. In one particular application the invention is directed to the detection of bone, including bone fragments, in chicken meat.

During manufacturing or processing, the presence of foreign material is a persistent problem. Foreign material is sometimes accidentally introduced into a process stream, for example when small objects or contaminates fall into a process stream. Foreign material also occurs more naturally, such as when components of the raw materials are separated or otherwise processed and one type of component is inadequately removed. Examples of this latter type are prevalent in the food processing area, and include the undesirable presence of bone, cartilage, pits, seeds, cores, or any other similar objects either in whole or fragmentary form in a stream of foodstuffs. Regardless of the foreign object source, it is generally desirable to detect and/or remove any foreign material to assure the quality and safety of the resulting product.

It is therefore an object of the present invention to provide a system and technique for detecting foreign material. Further, because traditionally it is more difficult to differentiate between foreign material and heterogeneous bulk material, it is a further object to provide systems and techniques that are operable to detect foreign material in an otherwise heterogeneous material. It is also an object to provide systems and techniques operable to detect foreign material in a process stream and to remove the foreign material from the process stream. It is a further object to provide systems and techniques that can reliably detect foreign material in a rapid and cost effective manner. It is a still further object to provide a novel method for the determination of other properties of a materials, such as the characterization of the degree of mixing or inhomogeneity in an inhomogeneous system. One or more of these or other objects are met by various embodiments of the present invention.

SUMMARY

The present invention provides novel systems and techniques for detecting foreign material utilizing either optical backlighting or ultrasonic inspection or a combination thereof.

In one aspect, the present invention provides novel systems and techniques for detecting the presence of bone or other foreign material in meat with optical backlighting. In one form, a shadow image of the bone is detected when the meat is optically backlit with source light having a wavelength between about 500 nm and about 600 nm. The source light can be substantially monochromatic light. In one refinement, a process stream of the meat is conveyed between first and second opposed walls substantially transparent to the source light and comprising a portion of an optical inspection station. The process stream can be confined between the walls and in contact with the inner surfaces of the walls. In a further refinement or in other forms, the optical inspection station includes a planar array of LEDs for supplying the light to optically backlight a section of the process stream, a camera for capturing optically backlit images of the process stream, and a processing assembly for determining the presence of bone in the meat if at least a portion of the captured image exceeds a predetermined threshold. In a further refinement or in other forms, the images are captured at a rate sufficient for an individual bone to be detectable in multiple captured images as the bone passes through the optically backlit section of the process stream and the presence of bone is determined if a portion of more than one of the captured images exceeds a predetermined threshold. Multiple inspection stations can be provided in series with optical backlighting occurring from different sides of the process stream at the successive stations. The optical backlighting can be performed alone or in combination with other detection techniques, such as one or more of the ultrasound interrogation techniques also described herein.

In one ultrasound interrogation technique, a process stream is interrogated with pulses of a limited extent sound field spanning a portion of the stream. The off-angle scattering response to the interrogating is then detected with a plurality of spaced receivers, with the presence of foreign material determined from the received response. In one refinement, the ultrasound receivers are focused on different sections of the insonified field and provide an indication of the relative location of detected foreign material in the process stream. In other refinements at least two ultrasound receivers are focused on overlapping sections of the insonified filed but are oriented at substantially different angles to a common interrogation axis.

Another embodiment of the invention provides a novel technique for the detection of foreign material in a product including interrogating the product with ultrasound and determining the presence of foreign material based on the detected off-angle ultrasound scattering response. In further refined embodiments, the detected scattering response is compared to a threshold to determine the presence of foreign material. In other embodiments, the detected response from a plurality of off-angle detectors are used to determine the presence of foreign material. In still further refined embodiments, the inventive technique is used to detect foreign material in flowing inhomogeneous process slurries, and/or the technique is used to detect foreign material in foodstuffs.

Also provided is a novel system including a conduit defining a flow path with a generally rectangular cross section, one or more inspection devices operable to transmit ultrasound to interrogate a process stream in the generally rectangular portion of the flow path, a plurality of spaced receivers each operable to receive an off-angle ultrasound scattering response to interrogation with the ultrasound; and a processing device operable to determine presence of a foreign material in the process stream based on a comparison of the off-angle ultrasound scattering response to a predetermined threshold.

Also provided is a novel system comprising a conduit operable to receive a process stream, one or more inspection devices operable to interrogate a volume of material in the process stream with ultrasound, at least two receivers focused on substantially non-overlapping interrogated volumes of material each operable to receive an off-angle ultrasound scattering response to the interrogation; and a processing device operable to determine presence of a foreign material in the process stream and to provide an indication of the spatial location of the foreign material in the process stream based on a comparison of the off-angle ultrasound scattering response of each receiver to a predetermined threshold.

BRIEF DESCRIPTION OF THE DRAWINGS

FIG. 3 is a top view of the FIG. 2 inspection station.

FIG. 4 is a top view of an alternative configuration for the inspection station of FIG. 2.

FIGS. 7A and 7B are side and sectional views respectively of yet another alternative configuration for an inspection station.

FIG. 10 is a schematic illustration of an optical backlighting system.

DESCRIPTION OF PREFERRED EMBODIMENTS

Figure 1:
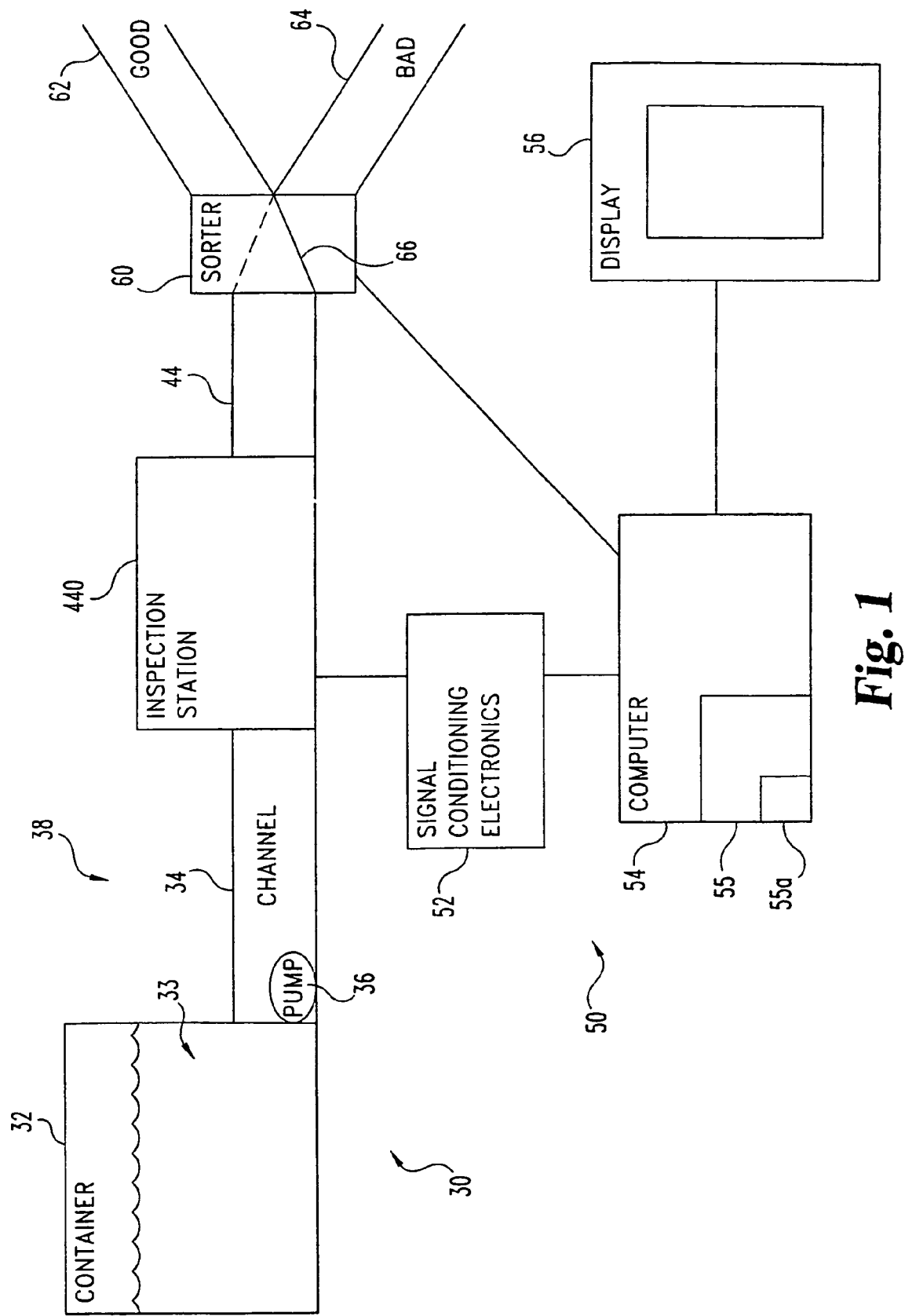
FIG. 1 is a schematic illustration of a processing system according to an embodiment of the present invention.

For the purposes of promoting an understanding of the principles of the invention reference will now be made to the embodiments illustrated in the drawings and specific language will be used to describe the same. It will nevertheless be understood that no limitation of the scope of the invention is thereby intended. Any alterations and further modifications in the illustrated embodiments, and any further applications of the principles of the invention as illustrated herein are contemplated as would normally occur to one skilled in the art to which the invention relates.

Turning now to FIG. 1 a processing system 30 for determining the presence of foreign material is depicted. System 30 includes a material supply container 32, an inspection station 440, and a sorting station 60. System 30 also includes a conveyor assembly 38 for transporting the bulk process material 33 from container 32, through inspection station 440 to sorting station 60. System 30 is adapted to interrogate a bulk fluid material, and conveyor assembly 38 includes channel 34 and pump 36 operative to pump material 33 through inspection station 440 and to sorting station 60 via channel 44.

At inspection station 440, the bulk material 33 is interrogated with ultrasound. The bulk material 33 interacts with the ultrasound and in response to the interaction scatters ultrasound in various directions. A portion of this scattered ultrasound (the scattering response) is detected by ultrasound receivers. Station 440 is electrically connected to processing assembly 50, which includes signal conditioning electronics 52, computer 54, and display 56. Assembly 50 receives a signal representative of the scattering response and determines the presence of foreign material in bulk process material 33 based on the received scattering response. Assembly 50 also is connected to sorting station 60 for operation of diversion valve 66. Valve 66 normally directs the bulk material 33 down channel 62. However, when bulk material 33 is determined to contain foreign material, valve 66 is operated to direct at least a portion of the bulk material 33 containing the foreign material down channel 64.

Figure 8A:
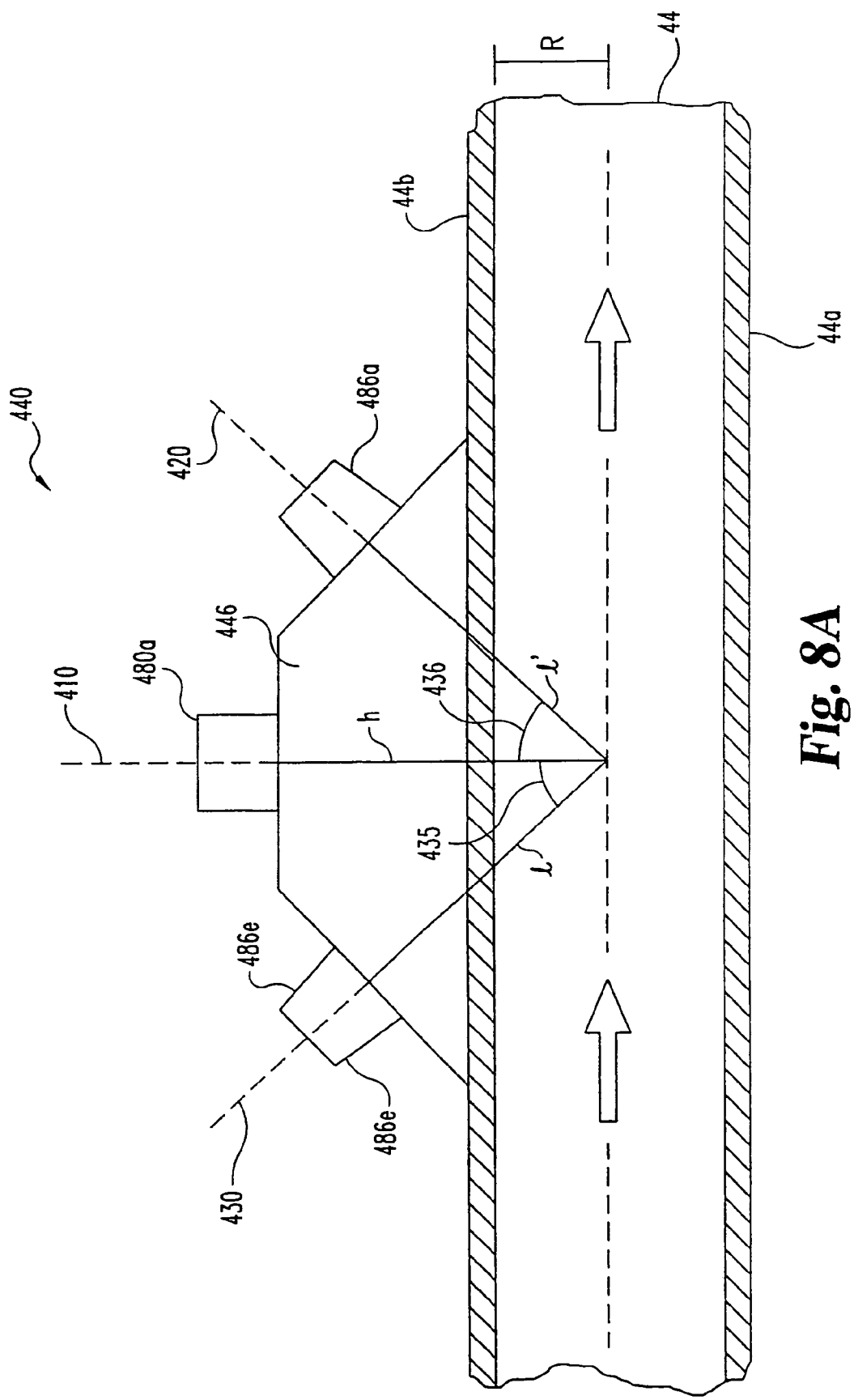
FIGS. 8A and 8B are side and top views respectively of the inspection station utilized to perform the experimental example described hereinafter.
Figure 8B:
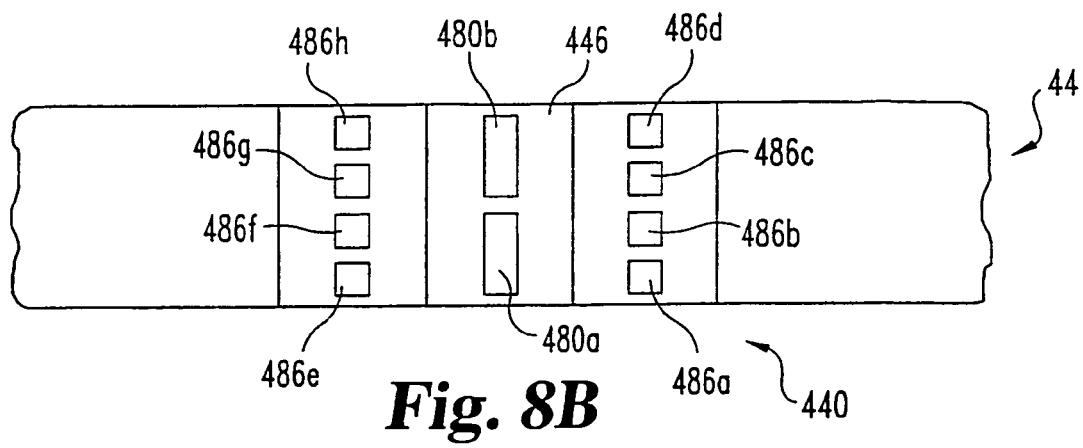

Turning now to FIGS. 8A and 8B, more particular features of inspection station 440 are illustrated. Station 440 includes a pair of ultrasound transmitters 480*a* and 480*b* and a plurality of ultrasound receivers 486*a*-486*h*. Transmitters 480*a* and 480*b* are mounted to the upper surface of solid wedge piece 446 and aligned parallel to interrogation axis 410 perpendicular to the flow direction. Receivers 486a-486h are mounted to the angled sides of wedge piece 446 and are aligned parallel to detection axes 420 and 430. Wedge piece 446 serves as a solid acoustic couplant between the ultrasound inspection devices and the process stream.

Channel 44 is rectangular in cross section, and both wedge piece 446 and upper wall 44b of channel 44 are of uniform thickness across the width of channel 44, providing a generally uniform acoustic pathlength for sound coupled into and out of channel 44. Preferably, both wedge piece 446 and wall 44b of channel 44 are formed of the same solid material such as stainless steel, Plexiglas, Lucite, or polysulfone. Piece 446 and wall 44b together form an acoustic path for ultrasound to travel from transmitters 480a and 480b to the contents of channel 44, and also for the scattering response to travel from channel 44 to receivers 486a-486h. In a preferred embodiment, wedge piece 446 is integral with upper wall 44b, where it is to be understood that the integral unit can be formed by machining or molding the components as a unitary structure. In alternative embodiments, wedge piece 446 is bolted, glued, or otherwise affixed to wall 44b.

Figure 9A:
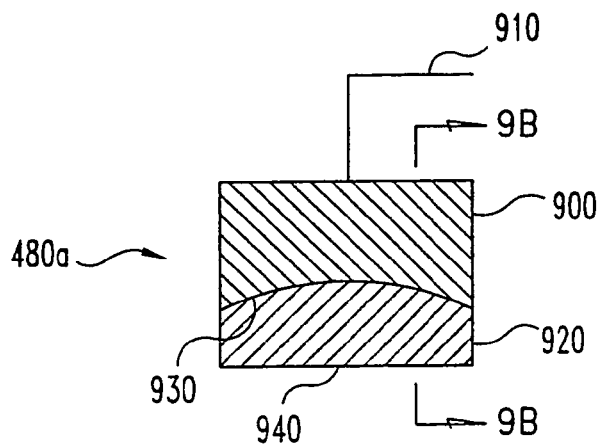
FIGS. 9A and 9B are side sectional views of a cylindrically focused inspection device.
Figure 9B:
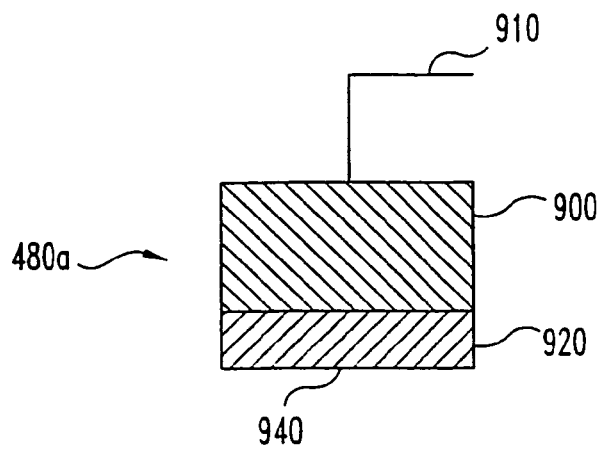

Each of the transmitters 480a and 480b are elongated and placed end-to-end to generally span the width of channel 44. In one aspect, they extend beyond the opposite sidewalls of the channel. In operation, transmitters 480a and 480b produce a sound field in channel 44. In one aspect, the produced sound filed is of limited extent and/or does not substantially diverge in the area of interest. In the illustrated embodiment, the area of interest is the channel 44. In one particular aspect, the produced sound field is convergent in at least one dimension in the area of interest. Transmitters 480a and 480b may be each cylindrically focused, as shown in FIGS. 9A and 9B, to produce a focused sound filed, which is one form of a sound filed that is convergent in at least one dimension. In such an embodiment, transmitter 480a includes an ultrasonic transducer 900 with signal line 910. Transducer 900 has a cylindrically concave face 930 configured to produce a cylindrically focused sound field. A correspondingly convex acoustic coupling 920 and/or delay material is provided in contact with the concave face 930 of the transducer 900 so as to provide a transducer assembly with a generally flat outer surface 940 for placement adjacent the flat outer surface of wedge piece 446. It is also contemplated that wedge piece 446 could include a correspondingly convex surface with coupling 920 omitted. Alternatively or in addition, other acoustic coupling materials, such as a gel, could be provided between transducer 900 and piece 446 to form the desired acoustic transmission paths. In one alternative embodiment, a single transmitter is used in place of the two transducer arrangement. In another alternative embodiment, transmitters 480a and 480b are placed in a staggered, rather than end-to-end, orientation.

The receivers 486a-486h may also each be cylindrically focused and can be configured similar to transmitter 480a, spanning generally the entire width of the channel or slightly beyond. Another example of a cylindrically focused transducer assembly useful in the present invention is given in U.S. Pat. No. 5,062,299 to Davis et al. which is hereby incorporated by reference in its entirety. In addition to or as an alternative to cylindrically focused transducer assemblies, spherically focused assemblies may be used as one or more of the transmitters (480a or 480b) and/or receivers (486a-486h). In still other embodiments, phased arrays of transducers or flat transducer elements in combination with an acoustic lens could be used to create focused acoustic sound fields. In other variations, a flat transducer element without focusing can be employed for one or more of the transmitters or receivers. It is to be understood that due to diffraction effects, flat transducers can produce a sound filed that is convergent in one dimension in the area near the transducer. When a flat transducer is used as a transmitter, it can be sized to produce a sound field convergent in at least one dimension in the area of interest (the channel 44).

In operation, transmitters 480a and 480b are simultaneously pulsed to produce a sound field in channel 44. As described above, in the illustrated embodiment transmitters 480a and 480b are cylindrically focused and produce a focused acoustic sound field in the channel 44. Signal conditioning electronics 52 (see FIG. 1) receive the response from the ultrasound receivers 486a-486h and include a time gate to select that portion of the signal representing the scattering response from material in channel 44. The gating parameters can be empirically determined by observing the scattered signal on an oscilloscope and selecting the portion of the signal between the reflections from the inside surfaces of upper and lower channel walls 44b and 44a respectively. Electronics 52 include an analog-to-digital converter to digitize the signal and pass the digitized scattering response to computer 54. Computer 54 contains memory 55 and transportable memory device 55a, such as an optical or electromagnetic disk, and includes programming instructions operable to cause computer 54 to process the scattering response in real time and determine the presence of foreign material based on that processed response.

In one embodiment of this processing, the presence of foreign material is determined by comparing off angle scattering response from the material in the inspection zone to an amplitude threshold set based on the response from "uncontaminated" material. If the scattering response signal exceeds this threshold, the suspected presence of a foreign material is determined. Alternatively, this comparison could be performed using analog signal processing techniques.

In one form, the scattering response from each of the plurality of receivers 486a-486h is provided to computer 54 through multiple, parallel signal channels. A background noise signal can be determined by averaging these signals over several clean runs of the bulk material without any foreign material in the stream. Alternatively, a background noise signal can be determined by maintaining a rolling average signal template of these signals under operating conditions, where the rolling average window is long enough to minimize any effects due to the infrequent occurrence of foreign material. Computer 54 then subtracts the background noise component from the received response. A separate background signal can be determined for each receiver 486a-486h to account for variations between receivers 486a-486h. After subtracting the background signal, computer 54 determines the maximum magnitude of the resulting signal and compares that maximum value to a threshold set for the associated receivers 486a-486h to determine the presence of foreign material.

In one preferred form, adaptive signal processing is used. In this form the background signal is a rolling average signal template determined under operating conditions. This rolling average signal will reflect changes in the operating conditions, such as changes in the temperature, composition, consistency, or degree of mixing of the bulk material. In one embodiment, changes in this rolling average signal are quantified and used to indicate corresponding changes in the composition or consistency of the bulk fluid either alone or in combination with foreign material detection.

When performing foreign material identification and/or detection according to the embodiments described herein, signal transforms can be performed between the time and frequency domains as would occur to those of skill in the art.

Figure 24:
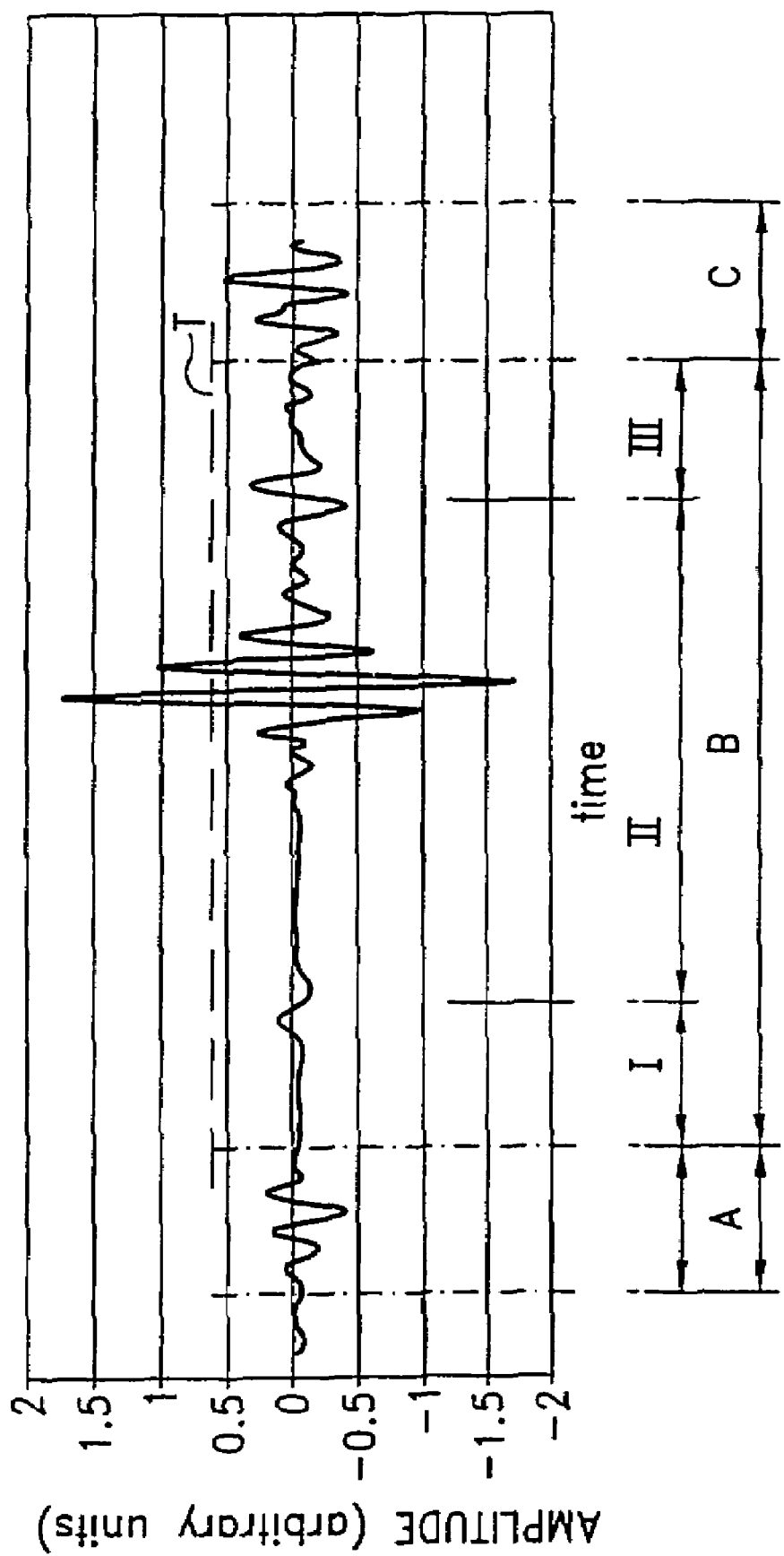
FIG. 24 is an exemplary plot of received signal amplitude versus time for the embodiment of, for example, FIG. 8A.

An exemplary off angle scattering response (amplitude versus time) at a receiver (for example receiver 486e in FIG. 8A) after a pulse interrogation is given in FIG. 24. The time response is gated into three main zones for processing, where the location of the time gates is determined as a function of the geometry and the materials of interest. Zone A is selected to correspond to the top wall (44b in FIG. 8A) interface echo, where the interface refers to the interface between the top wall and the channel contents. Under uniform flow in the channel, this should be a near constant signal and can be used to monitor for fault conditions, for example by monitoring the average peak amplitude. A large change in the Zone A response corresponds to a fault, such as the presence of a large air pocket or the absence of material in channel.

Zone B corresponds to scattering from inside the channel. This is the data that can be summed to provide the background for setting the amplitude threshold for foreign material detection. A large pulse, such as the one exceeding the exemplary threshold T, indicates foreign material. Zone B can be further time gated into sub-zones I, II, and III to determine the spatial depth location for the detected material. Sub-zones I and III correspond to the near front wall and near back wall regions respectively, and data from these near wall zones can be integrated with other inspection techniques, for example those that may be more sensitive to surface detection. For example, as described more fully below, it is contemplated that the near wall ultrasound data can be integrated with optical backlighting data to confirm targets detected in near-surface zones.

Zone C corresponds to the back wall response. The arrival time and amplitude of this gate data is extracted and used to determine information on the channel contents. A rolling average for both arrival time and amplitude are calculated with variations from the rolling average used to indicate fault conditions. A substantially uniform amplitude and arrival time corresponds to uniformity of the material flow through the channel. Changes in the arrival time indicate changes in the average speed of sound through the channel, and thus changes in the bulk properties of the material in the channel. Loss of signal or a large increase in signal amplitude indicates substantial change in material contents, such as a large air bubble.

The data from the three inspection zones (sub-zones I-III) are then combined with data from the other receiving transducers spanning the remainder of the flow path. Data from adjacent transducers provides information in patterns that is used to increase the probability of detection while reducing the chance of false positives, for example by assigning a higher probability that a given signal above the threshold is a result of foreign material when multiple adjacent transducers yield a similar signal. The data from the suite of transducers and multiple gates are taken at a pulse repetition frequency that gives data corresponding to volume elements that can be mapped on the channel contents by the computer 54. The pulse repetition frequency can be selected to repeat at least three times before a feature would pass completely through the inspected volume. The computer 54 can then fuse the elements for the generation of eject signals.

In another embodiment, the scattering response is compared to entries in a library of different scattering responses for similar material of known content. In this manner, characteristics of the process stream can be determined when a detected scattering response matches one in the library. Other approaches may also be employed such as comparison of the received response to a scattering model and/or use of a neural network to recognize features in the scattering response.

Once the suspected presence of foreign material is determined with computer 54, computer 54 (or a different controller) provides a corresponding indication on display 56 and sets a detection flag. Optionally, the location of the foreign material in the process stream can be indicated. Computer 54 generates one or more control signals (eject signals) to operate diversion valve 66 to divert the contaminated product from the stream, calculating the appropriate travel time from inspection station 440 to valve 66 with flow information obtained from, for example, a conventional flow meter (not shown). Multiple diversion valves 66 configured to select portions of the flow channel can be utilized, with the eject signals assigned to particular valves 66 or diverters based on the detected spatial location of the defect. It is to be understood that integrated circuit microcontroller or one or more programmable logic controllers (PLCs) can be used in place of computer 54.

In a particular embodiment, sets of receivers 486a-486h are focused on overlapping insonified volumes of material in the channel 44. For example, in FIG. 8A receivers 486a and 486e are focused on overlapping volumes. The scattering response of each of multiple receivers 486a-486h to the same interrogation pulse can then be compared to associated thresholds for each of the multiple receivers 486a-486h. When a predetermined number of receivers focused on overlapping volumes produce a response to the interrogation pulse exceeding the predetermined threshold, for example 2 of such receivers, foreign material is determined to be present. By employing multiple receivers trained on overlapping volumes, the occurrence of false positives can be reduced and/or the sensitivity of each receiver can be increased, for example by reducing the threshold for that receiver.

It should also be understood that certain different receivers can be arranged to be trained on substantially different volumes. For example, as shown in FIG. 8B receivers 486a and 486h are focused on non-overlapping parts of channel 44. By examining the response from these non-overlapping receivers, the relative location of foreign material in stream 44 can often be determined with greater resolution, facilitating diversion of a relatively smaller portion of the process stream.

While not intending to be bound by any theory of operation, the off-angle scattering response differentiates between scattering targets in the bulk process stream and the foreign material to be detected because of contrast between acoustic impedance, particle size and/or shape verses that for the background matrix of the bulk material. Scattering by targets with significant contrast in terms of acoustic impedance, hardness, size, and/or shape can be expected to scatter ultrasound at higher intensities and over larger angles than from targets that form the background matrix. The orientation of irregularly shaped particles can also influence the scattering response. The differential response between objects with acoustic impedance contrast when compared to the surrounding medium is preferably achieved by control of composite ultrasonic sound fields. The composite sound fields are determined by the particular ultrasound transducer specifications as well as its fixed spatial configuration.

The fixed spatial configuration is defined by the angles 435, 436 (see FIG. 8A) the height of the transmitter, h, and the height of the receivers, l and l'. The heights h, l, and l' and the angles 435, 436 are relative to a coordinate system whose origin is in the vertical center of the process stream.

The transmitter height, h, is set so that the center of the transducer's focal zone is positioned in the vertical region of about 0 to 0.25 R, where R is the radius of the process stream (or half the thickness of the stream in the case of a rectangular channel). The receiver heights, l, and l' are set so that the center of the transducer's focal zone is positioned in the vertical region of 0 to 0.25 R. The size of the focal zones are selected to span the thickness of channel 44 and the axes of the transmit beam and the receiver beams lie in the same vertical plane. In the illustrated embodiment, the heights h, l, and l' are each about equal to the focal length of the transducer.

The angles 435, 436 are in the range of 18 degrees to 162 degrees. Selection of optimum angles is dependent on the selected inspection frequency, the transducer focal length, the geometry of the channel, and the size range of the foreign material sought to be detected in the process stream. The interrogation frequency to be employed can be determined empirically using a representative sample of the process stream medium containing no extraneous materials. Preferably a high frequency is used that does not result in root mean squared (RMS) variation of 0.5 or more across a representative portion of the process stream. A typical representative portion might be a lateral aperture of at least 10×D, where D is the dimension that approximates the graininess of the medium. The angles 435, 436 can then be determined empirically using a representative sample of the process stream medium containing a foreign object whose size and acoustic impedance is representative of foreign objects to be detected. The angles 435, 436 are preferably adjusted in the range of 18 degrees to 162 degrees until the scattered signal amplitude is at least 6 dB above RMS background signal.

It is expected that the optimum inspection frequency and angles will vary according to the process stream being inspected. It has been found that for a process stream of whole chicken breast meat slurry, a frequency of 1.0 MHz with the angles 435 and 436 between about 15 and 45 degrees, for example between about 15 and 35 or between about 18 degrees and 22 degrees, provides acceptable results for a 1 inch channel thickness (2R) and transducers with 2 inch focal lengths.

While as illustrated in FIG. 8A angles 435 and 436 are substantially identical, they can be different. In one variation, the location of the transmitters 480a and 480b and one set of the receivers (for example receivers 486a-486d) on piece 446 are switched. In this configuration, axis 420 would become the interrogation axis and axis 410 would be a detection axis. Accordingly, the corresponding angles between the interrogation and detection axis would be substantially different for the two sets of detectors, for example varying by a factor of about two. In embodiments where multiple receivers are oriented along axes defining substantially different angles with a common interrogation axis, the different receivers may be preferentially sensitive to the detection of different types of object, for example those having different shapes and/or relative configurations. For example high aspect ratio particles (or such as bones in meat) may scatter ultrasound with greater intensity at different angles depending on the orientation of the particles (long axis parallel or perpendicular to the flow direction). Use of receivers at different relative angles to a common interrogation axis can improve detection performance. Relative angles of about 30 and about 60 degrees is one acceptable such dual angle configuration for detecting bones in a chicken breast slurry.

Figure 2:
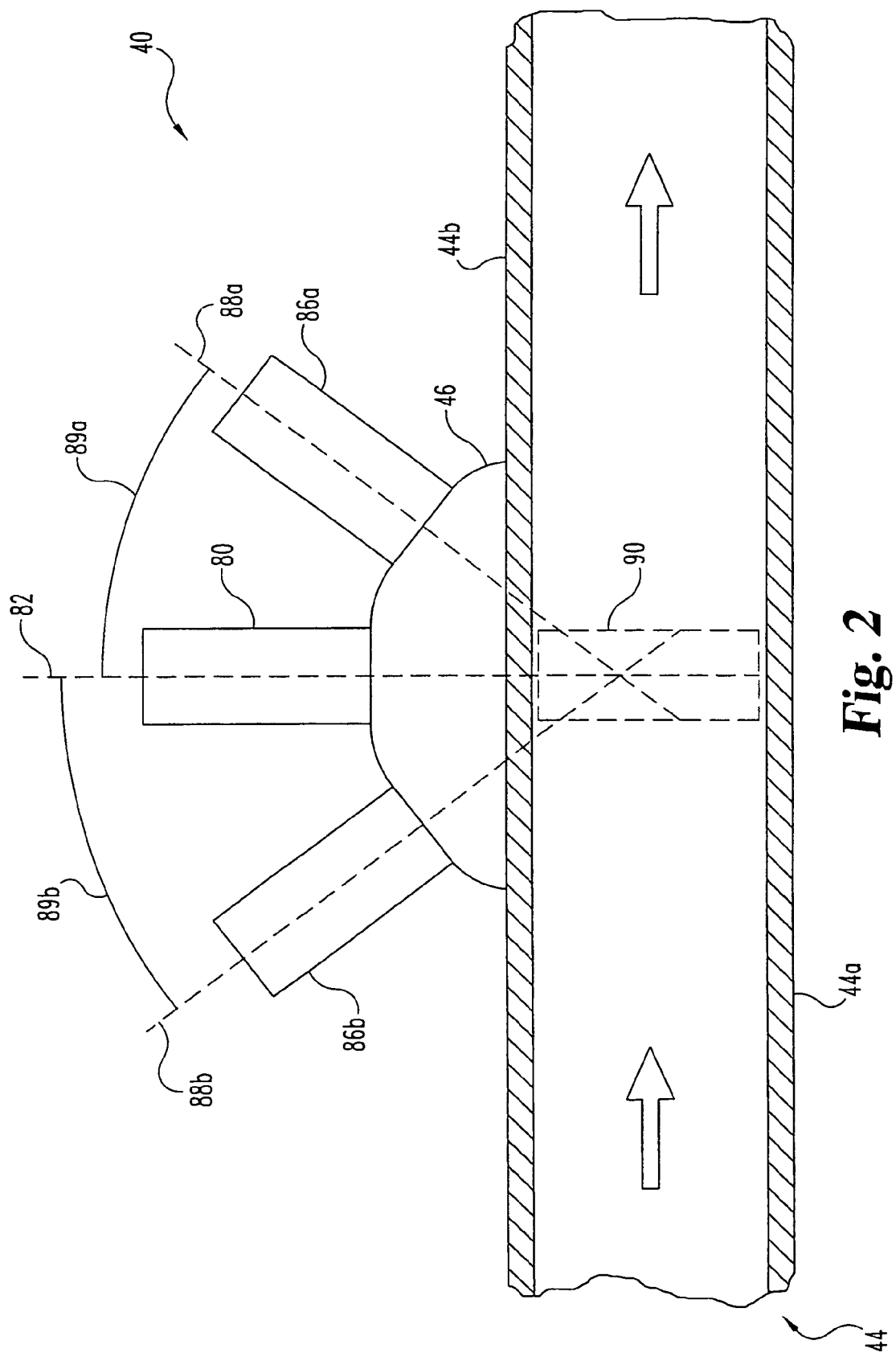
FIG. 2 is a side sectional view of an inspection station for the system of FIG. 1

Turning now to FIG. 2, an alternative configuration for inspection station 440 is illustrated. It is to be understood that inspection station 40, like the all other inspection stations presented herein, can be used in place of station 440, with corresponding adjustment to signal processing based on any transmitter and receiver differences. Station 40 includes an ultrasound transmitter 80 and ultrasound receivers 86a and 86b. Transmitter 80 is aligned along an interrogation axis 82 to deliver ultrasound energy to an inspection zone 90 in the bulk material 33 contained in channel 44. Ultrasound receivers 86a and 86b are arranged to detect the off angle scattering of ultrasound from zone 90. Both transmitter 80 and receivers 86a and 86b are arranged above the closed channel 44 in contact with a solid acoustic couplant 46. In one mode of operation, a pulse of ultrasound from transmitter 80 travels through couplant 46 and the upper portion 44b of channel 44 before entering zone 90. Scattered ultrasound emanating from zone 90 then travels through portion 44b for detection by receivers 86a and 86b.

As depicted in FIG. 2, detector 86a is aligned along detection axis 88a and detector 86b is aligned along detection axis 88b. Axes 88a and 88b each intersect zone 90 and axis 82. Detector 86a is aligned at an angle 89a with respect to interrogation axis 82, and detector 86b is aligned at angle 89b. Each angle 89a or 89b defines a relationship between transmitter 80, zone 90, and receiver 86a or 86b and thus can range from zero to 180 degrees. While axes 88a and 88b each intersect axis 82 as illustrated, it is understood that one or more of the axes can be skewed relative to axis 82, the angles 89a and 89b then being defined by the intersecting projections of the skew axes.

Turning now to FIG. 3 and with continued reference to FIG. 2, a top view of inspection station 40, looking down interrogation axis 82 is illustrated. Inspection station 40 includes additional detectors 86c and 86d aligned about ultrasound transmitter 80. Detectors 86a-86d are approximately equally spaced about interrogation axis 82 such that the angle 92 between the detection axes is about 90 degrees.

FIG. 4 depicts an alternative inspection station arrangement. Inspection station 140 is otherwise identical to station 40 save that each detector 86a-86d is rotated about 45 degrees about the interrogation axis 82. An appropriate acoustic coupling agent (not shown) is provided between channel 44 and each of transmitter 80 and receivers 86a-86d. Whereas in station 40 the detection axes had projections into the flow path that were approximately parallel or perpendicular to the bulk material flow (indicated by arrows), the detection axes in station 140 have projections that are at about 45 degree angles to the flow direction.

Figure 5:
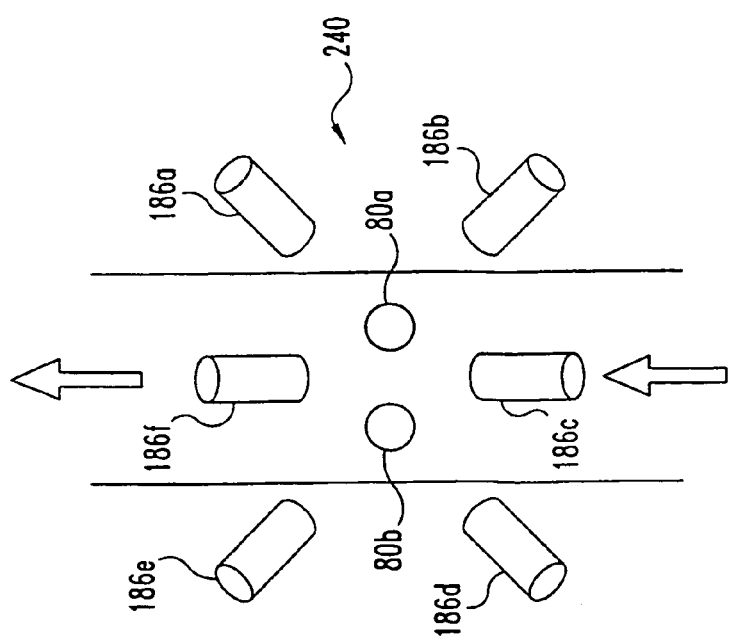
FIG. 5 is a top view of a further alternative configuration for an inspection station.

Turning now to FIG. 5, a still further embodiment of an inspection station is depicted. Station 240, like station 140, can be used in place of station 40. Station 240 includes a pair of ultrasound transmitters 80a and 80b with parallel interrogation axes. Each of the interrogation axes of transmitters 80a and 80b are also aligned in a plane perpendicular to the flow direction the material in channel 44. A plurality of receivers 186a-186f are aligned around the transmitters with their detection axes at angles relative to the each of the interrogation axes. As described above, an appropriate acoustic coupling agent (not shown) is provided between channel 44 and each of the transmitters and receivers.

Figure 6A:
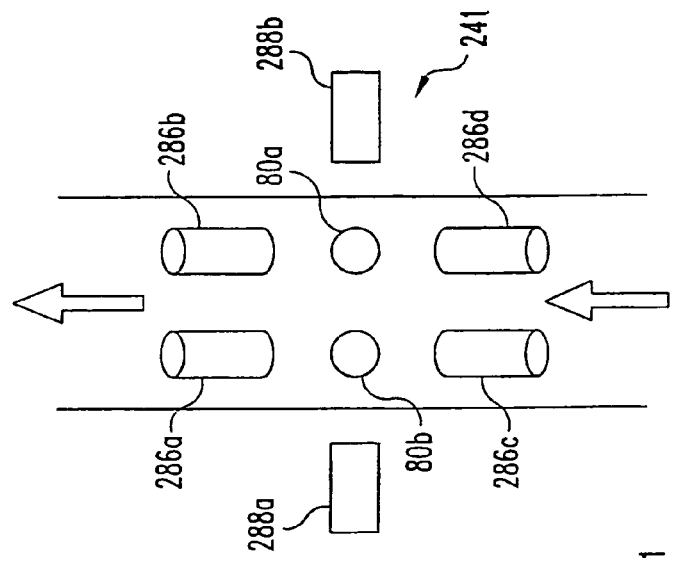
FIGS. 6A and 6B are top and side views respectively of still another alternative configuration for an inspection station.
Figure 6B:
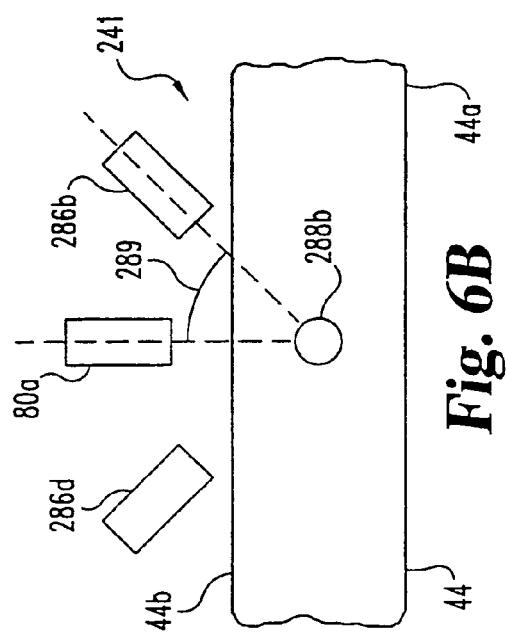

FIGS. 6A and 6B illustrate a still further embodiment of an inspection station. Like station 240, inspection station 241 includes multiple transmitters 80a and 80b surrounded by multiple receivers 286a-286d, 288a and 288b. Receivers 286a-286d are each above the top portion 44b of flow channel 44 and aligned at angle 289 relative to the interrogation axis. Angle 289 is, for example, approximately 45 degrees. Receivers 288a and 288b are at the sides of channel 44 with their detection axes at approximately a 90 degree angle to the interrogation axes.

A still further variation of an inspection station is depicted in FIGS. 7A and 7B. Station 242 differs from the previous stations 40, 140, 240, 241, 440 in that the transmitter 301 and receivers 310, 320, 330, 340, 350, are formed integrally with the conduit 305 for carrying the bulk material 33. Each transmitter 301 includes associated receivers 310, 320, 330, 340, 350 forming a transmitter/receiver set in a common plane perpendicular to the flow direction. Several transmitter/receiver sets are located at spaced locations along the length of the conduit 305, with adjacent transmitters 301 at different angular positions about the flow direction to reduce the effect of any dead spots at any one transmitter/receiver set location.

The provision of successive transmitter/receiver sets at varying angular orientations can also be employed for any of the aforementioned inspection stations 40, 140, 240, 241, 242, 340. Inspection stations 40, 140, 240, 241, 242, 440 can also each be employed singly or in combination with one or more other inspection stations 40, 140, 240, 241, 242, 440. Furthermore, it is to be understood that each of the transmitters and receivers in stations 40, 140, 240, 241, 242 are preferably, though not essentially, either cylindrically or spherically focused as described above with respect to station 440.

One particular application of the present inventive techniques is to detect the presence of harder objects, such as bones or bone fragments, in a process stream. However it is contemplated that other scattering targets, for example a latex glove in a process stream of foodstuff or other material can be detected according to the principles of the present invention. A still more particular application is to detect the presence of foreign material in an highly heterogeneous process stream or one in which multiple diverse scattering targets are normally present.

A particular example of the detection of harder objects in a heterogeneous process stream is presented below with respect to the detection of bone in chicken meat. A typical process stream in the poultry application includes a slurry of liquid and chicken breasts. The interface between the breasts and the liquid is an ultrasound scattering surface, and inhomogeneities in the chicken breasts themselves, for example flesh features (filaments and bundles in the meat muscle), can be ultrasound scattering sources. However, bone is harder and has a different size and shape than the chicken breast or the carrying liquid and the scattering at a given off-angle attributable to bone is adequately detectable over the scattering at the same given off-angle attributable to the bulk chicken breast tissue or tissue liquid interfaces.

The exact angle of the detected off-angle scattering response optimally suited for any particular application will likely vary for different applications of the present invention. Nonetheless, it is expected that scattering angles of between 10 and 55 degrees will be useful for many applications of the present invention.

In addition, the selection of the inspection frequency can provide balance between needed scattering response to foreign material with minimized sensitivity to other benign structures in the bulk flow. In the chicken meat examples presented below, the inspection frequency of 1 MHz corresponds to a wavelength of about 1.5 mm in tissue. This wavelength is comparable with the longest length dimension for bone fragments of interest. Wavelength to target maximum dimension ratios are preferably between 0.5 and 5, and more preferably are at least one.

In carrying out the present invention, ultrasonic signals having a frequency in the range of about 0.1 to 50 MHz may be employed, with signals in the range of 0.1 to 5 MHz being preferred. For certain embodiments, it is desirable to have the ultrasonic wavelength within the described ratio limits of the size of the foreign object to be detected.

Further, when implementing the present invention in fixed relation to a moving material, for example detecting foreign material in a flowing process stream, it is desirable to sequentially and rapidly interrogate the material to increase the probability of foreign material detection. A suitable signal pulse repetition rate may be on the order of 30 to 850 pulses/second, with a range of 250 to 850 pulses/second being preferred for material flowing at a speed of about 30 cm/sec.

Various types of ultrasound transmitters and receivers are useful in practicing the present invention including both piezoelectric, electro-magnetic-acoustic transducers (EMAT), magnetostrictive transducers, laser-ultrasound, and magnetoelectric transmitters and receivers. These may be obtained from conventional ultrasound suppliers such as NDT Systems located in Huntington Beach, Calif., and Parametrics located in Boston, Mass. and Xactec located in Pasco, Wash.

A variety of cooked and uncooked foods may be inspected in accordance with the present invention, especially those in which water is present as a continuous phase constituting, for example at least about 30% or more by weight thereof. Non-limiting examples of foods suitable for inspection in accordance with the invention include, minced or strained baby foods, (e.g. meats, fruits, vegetables, and mixtures thereof), bologna, sausage fillings, liverwurst, frankfurter meat and the like, tomato ketchup, gruel, puddings, and soups. In addition, pitted or sectioned foods such as olives, peaches, pears, pineapple, prunes, and cherries, in whole or sliced form, suspended in a continuous liquid medium such as water, sugar syrup, or olive oil, may be inspected for the presence of pits, seeds and stems. Similarly, whole fruits and vegetables such as onions and potatoes may be immersed in a continuous liquid transport medium (such as water) and non-intrusively inspected for homogeneity, e.g., for the presence of rotten cores, embedded solids, or other internal abnormalities.

Advantageously, highly heterogeneous foodstuffs may also be inspected in accordance with the present invention. For example, inspection for unremoved pits in cherries suspended in water. In addition, plums, olives, pears and other whole and halved fruits may similarly be inspected.

Although most preferably applied to human and animal foodstuffs (including beverages, e.g., milk, alcoholic beverages, and soft drinks), the apparatus and process of the present invention may advantageously be utilized to inspect a wide variety of other substances. In one preferred alternative embodiment, the inspected material will be a fluid, which can include a fluid suspension or slurry material. Thus, among the various materials which may be inspected are liquid, pasty, or highly viscous substances including without limitation petroleum products such as gasoline, motor oil, waxes and greases. Additional materials for inspection include various chemicals solvents, liquid household products, polymer streams, and the like.

It is to be understood that the present invention is applicable to a wide variety of processing environments. For example, in addition to the inspection of flowing or otherwise pumpable process streams, where conveyor assembly 38 is based on a pump and conduit, material carried on any other type of material conveyor can also be interrogated. Alternatively or in addition to use of the invention in conjunction with moving process streams, the invention is applicable for example to monitor a material in a batch process.

It should be further understood that the presence of foreign objects in a bulk material is only one property measurable in accordance with the present invention and that the present invention can be applied to measure other material properties. For example, the present invention can be used to quantify the degree of mixing in a fluid material by determining the nature or amount of inhomogeneity in the material. In this case, the relative amount of ultrasound off-angle scattering provides a measure of the degree of inhomogeneity in the material. Another application includes determining a material transition, such as the onset of crystallization or a change in average particle size in a suspension or slurry. In this application, a material can be substantially continuously monitored for a change in the off-angle scattering response, which change would be used to determine the onset or degree of transition.

Additional inspection of material in the process stream can also be utilized to supplement or complement the detection achieved according to the ultrasonic techniques described herein. Optical backlit information can be used with or without the ultrasound off-angle scattering data to determine the presence of foreign material in a process stream. It has been found that optical backlighting is particularly effective in detecting surface bones or bone fragments in meat. It has also been found that the ultrasound scattering technique is particularly effective at detecting buried bones. Accordingly, in a preferred alternative embodiment, both the backlighting technique and the ultrasound scattering technique are used where the combination of the two techniques is surprisingly effective in detecting foreign material. Other complimentary methodologies such as X-ray, electromagnetic, or electrical impedance analysis can also be employed either alone or in combination with any of the techniques described herein.

Turning now to FIG. 10, a schematic illustration of an optical inspection station 500 is depicted. In this optical inspection embodiment, computer 54 (or a plurality of computers in one or two way communication) receives the output of the optical inspection. In the chicken breast example, a portion 34 of the process stream upstream (or downstream) from station 440 is backlit with a light source 510. A suitable light source is a halogen lamp. A video camera 520 with a 550 nm bandpass filter 530 is then used to capture the image of the light that transmits through the chicken. It is to be understood that portion 34 of the process stream is constructed of appropriately transparent material, for example Plexiglas or polycarbonate, such that it passes light in the wavelength range of interest.

Surprisingly, it has been found that light in the preferred 500-600 nm wavelength range gives a high contrast between meat and bone. A more preferred range for chicken bone inspection is between 500 and 570 nm, for example 520-570 nm. Accordingly, computer 54, which preferably includes a frame grabber and processing instructions operable to processes captured backlit images of the chicken breast in real time, can readily determine the presence of bone. One method of computer determination is to perform threshold detection of the captured images, where the presence of a predetermined number of adjacent pixels in the captured image exceeding a threshold indicates the presence of bone. In one useful aspect, the predetermined number of adjacent pixels corresponds to a predetermined minimum physical size for a detected object to be considered a defect, for example at least about ⅛ inch by ⅛ inch. It is to be understood that a bone or other similar foreign object will show up as a shadow image and that, as used herein, exceeding a threshold includes both having a value numerically above a threshold value and having a value numerically below a threshold value. Alternatively or in addition a human operator can observe the backlight images to determine the presence of bone.

In one aspect, the light source 510 of optical inspection 500 is a substantially monochromatic light source. Substantially monochromatic light is light having a narrow spectrum, e.g. where a majority of the light from the source is contained in a relatively narrow bandwidth about a center wavelength, for example within about 50 nm or about 25 nm or about 10 nm of a center wavelength. Examples of substantially monochromatic light sources include light emitting diodes (LEDs) and lasers. Use of a monochromatic light source reduces or eliminates wasted light outside the wavelengths of interest for the optical detection. Wasted light is inefficient and can lead to undesirable heating of the process stream by the light source. Process stream heating can be particularly problematic for process streams of meat, because heating can cause premature cooking of the meat. When substantially monochromatic light is used, the filter 530 functions primarily to exclude ambient light. Filter 530 could be eliminated if ambient light is otherwise blocked, for example through the use of shrouding around the optical inspection station.

In one aspect the substantially monochromatic light source is an array of LEDs. The LEDs can be configured to provided a generally homogeneous light beam of a size and shape generally corresponding to the size and shape of the captured image. The light beam can be larger than the captured image to assure that the entire captured image is subject to the same light flux.

Figure 12:
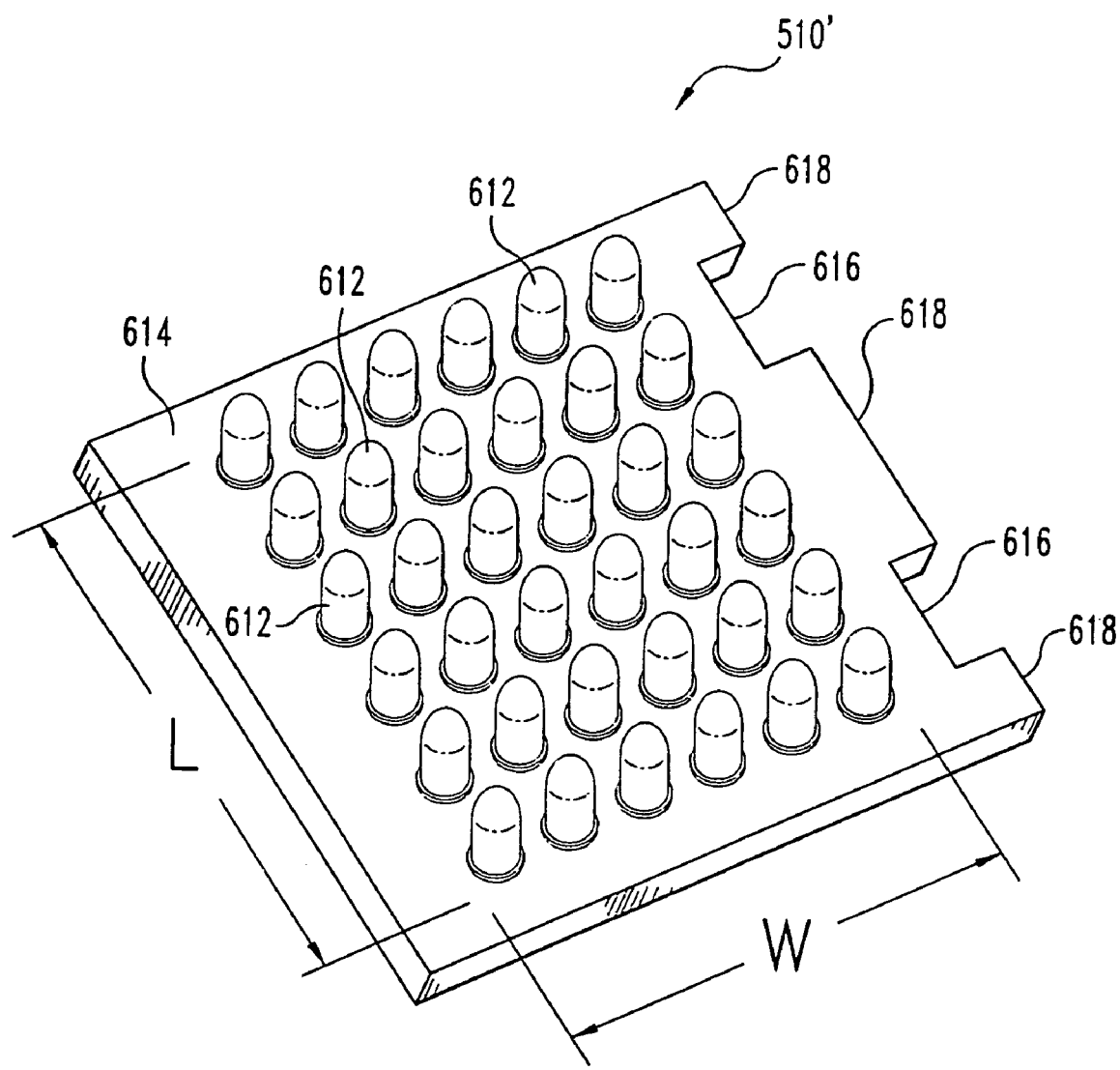
FIG. 12 is a perspective view of a LED array for optical inspection according to an embodiment of the present invention.

Turning now to FIG. 12, an exemplary light source 510' according to this aspect is depicted. Light source 510' includes a plurality of individual LEDs 612 densely packed to form an LED array. Useful LED arrays according to this aspect include LED spotlights. The individual LEDs are mounted on a common circuit board 614 to form a generally rectangular planar array having a length L and width W each about equal to the width of the flow path. As illustrated, the individual LEDs have a circular footprint and are symmetrically arranged on the circuit board 614 in rows and columns in a rectangular packing arrangement. Adjacent rows could be offset from each other to provide even closer packing density, for example as a hexagonal packing arrangement.

The densely packed individual LEDs 612 combine to provide a substantially homogeneous beam of light for optically backlighting the process stream. The properties of each LED and the packing density of the LEDs will determine the overall intensity of the light source 510', which can be selected to be any useful value sufficient to transmit a detectable amount of light of the appropriate wavelength through the process stream. One useful array is 700 LEDs packed in a 6 inch by 6 inch area where each of the LEDs are Model No. NSPG500S from Nichia America Corp. of Mountville, Pa., have a luminous intensity of about 11.6 candela (cd), 30° divergence, and produce green light at 520 nm. Other useful arrays might yield, for example, at least about 120 candela per square inch, for example between about 150 and 300 candela per square inch.

In another useful aspect, the light source 510' is mounted in close proximity to the process stream but is separated from direct contact with the transparent wall of the process stream by a flow path for a cooling fluid. In this configuration, a cooling fluid, such as air, can then be continually circulated over the light source and between the adjacent wall of the process stream to reduce any heating of the wall by the light source 510'. Reducing heating of the wall is one technique to reduce heating of the process stream.

Figure 13:
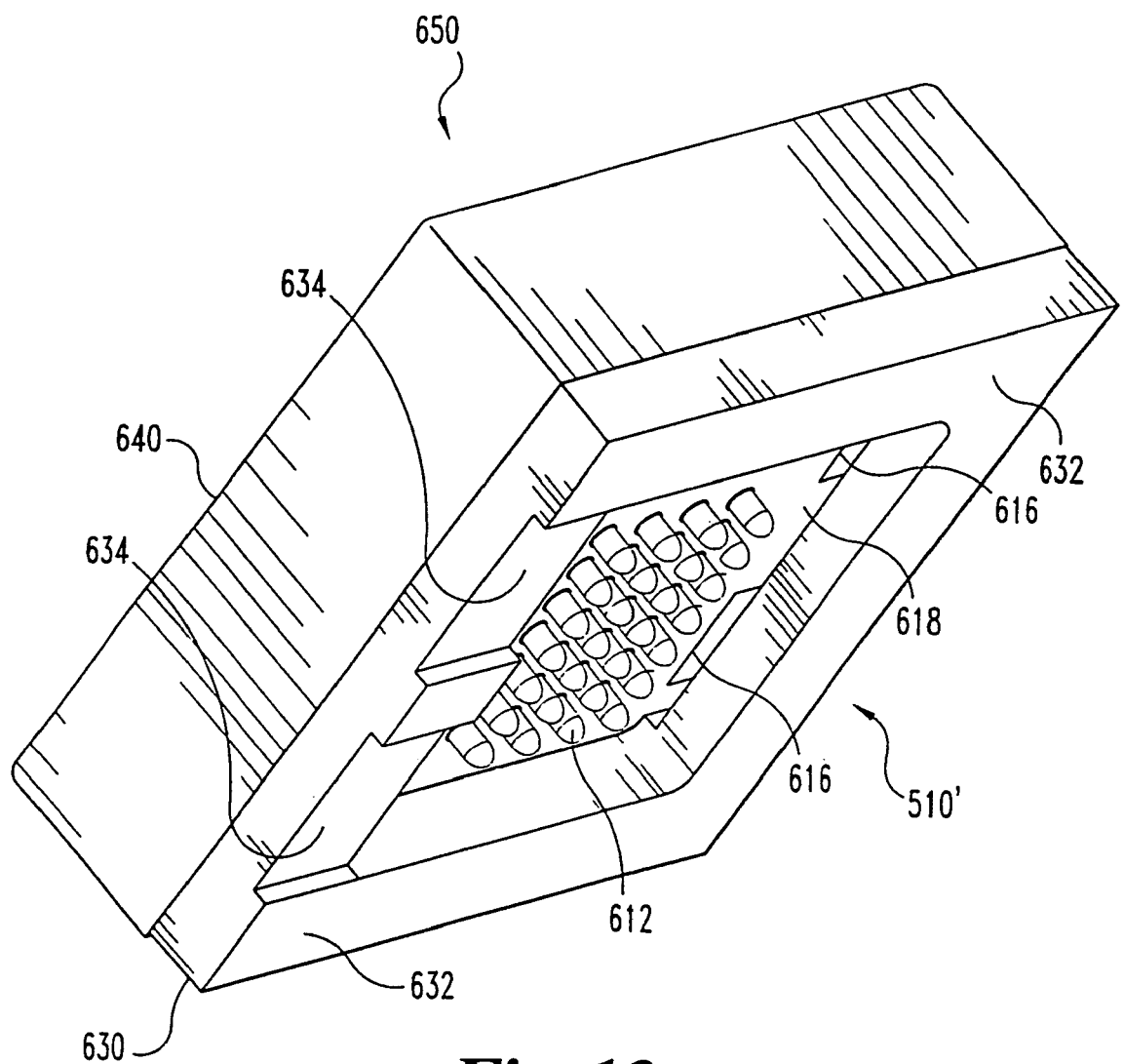
FIG. 13 is a bottom perspective view of the a light source assembly utilizing the LED array of FIG. 12.
Figure 14:
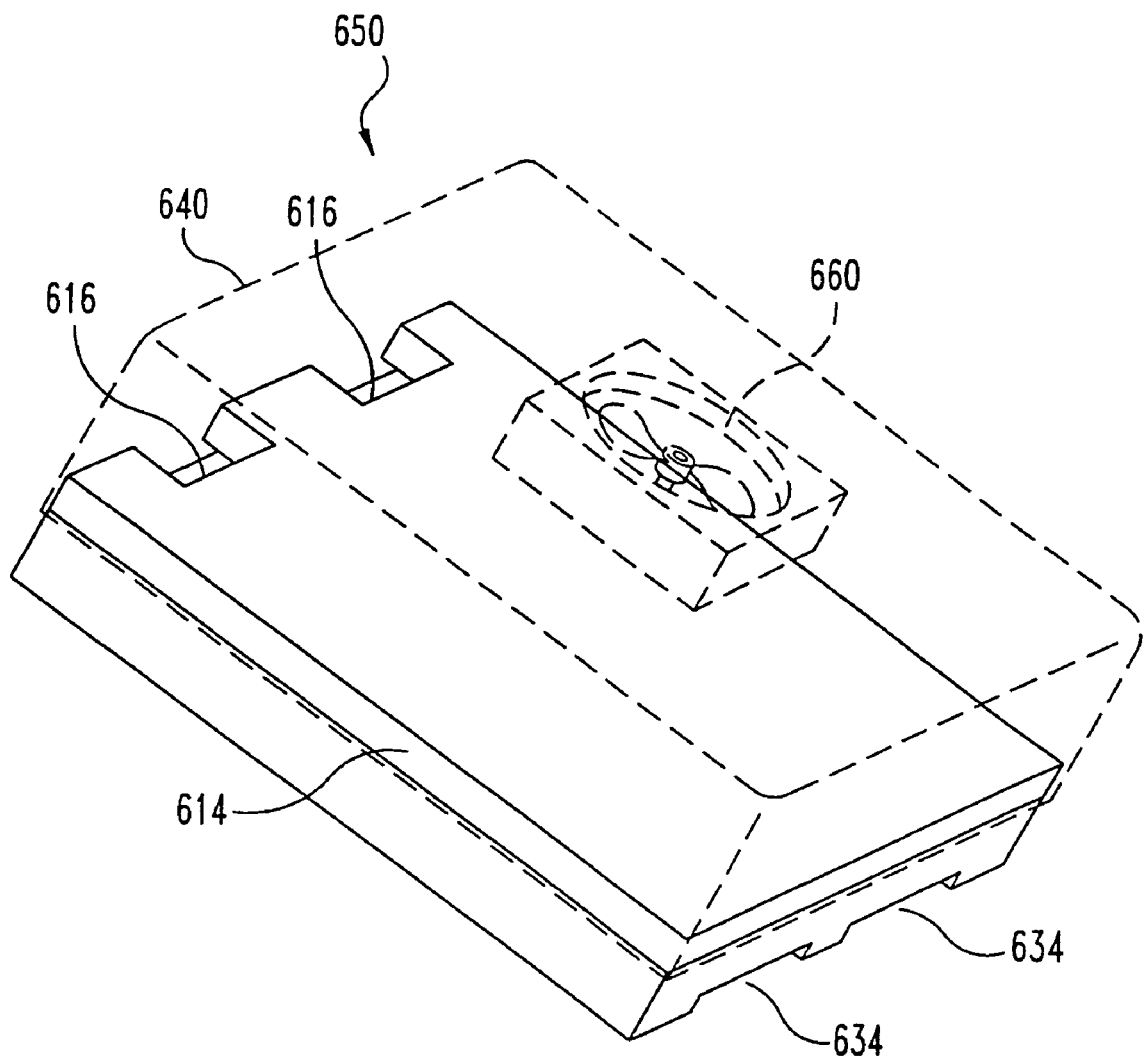
FIG. 14 is a top perspective view of the FIG. 13 light source assembly.
Figure 15:
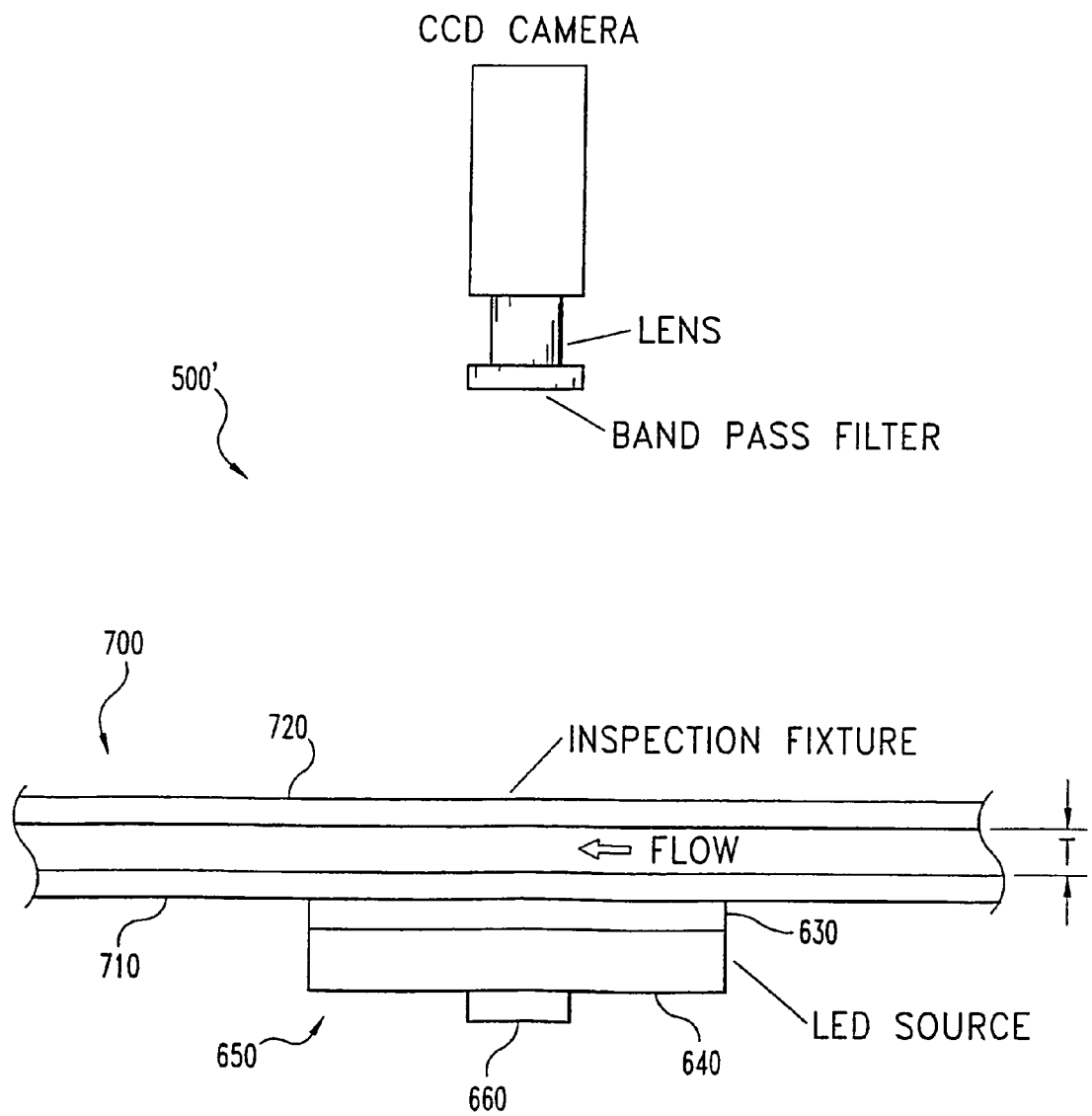
FIG. 15 is a schematic illustration of an optical backlighting inspection station utilizing the light source assembly of FIGS. 13 and 14.

Turning now to FIGS. 13-15 and with continued reference to FIG. 12, the light source assembly 650 is illustrated. Assembly 650 includes the light source 510' and a housing 640 mounted to a spacing plate 630. The spacing plate 630 is configured to be mounted to a transparent wall 710 or window 710 of an inspection fixture 700 with the perimeter face 632 of plate 630 in contact with the wall 710. A pair of openings 634 are provided on one side of the spacing plate 630 such that when the spacing plate 630 is mounted to the flat wall 710, the openings 634 define an air inlet into the assembly 650. A set of tabs 618 define openings 616 in the circuit board 614 of light source 510', and the light source 510' is mounted on the spacing plate 630 with the LED's 612 between the openings 616 in the circuit board 614 and the openings 634 in the spacing plate 630. The housing 640 covers the back side of the light source 510' and supports an exhaust fan 660 in a port of the housing 640. The fan 660 is operable to draw air through the cooling fluid flow path defined between openings 634 and 616 and out the back of the housing 630. In this manner, air is drawn across the LEDs 612 to remove the heat generated by the LEDs during operation.

The housing 640 and spacing plate 630 can be formed of any suitable materials, such as hard plastic or metals. The spacing plate is sized to maintain the LEDs 612 of the array a fixed distance from the adjacent transparent wall 710. A suitable distance is about 0.5 inches.

It has also been found that chicken meat is a good diffuser of light in the wavelength range of interest. Accordingly, the provision of an optical diffuser between the light source and the process stream is not necessary but could be employed. Regardless of whether a separate diffuser is utilized, diffusion of the light by the chicken meat will tend to obscure detection of bones buried deep in the chicken meat. To enhance the reliability of detection of all bones, the process stream is made thin in the inspection field (the zone examined by the camera). A useful process stream thickness for many applications will typically be less than about 2 inches, for example between about 0.25 and about 1.5 inches, where the thickness refers to the thickness of the meat product and any accompanying conveying fluid (if applicable) through which the light will travel.

The thickness of the process stream can be controlled in any conventional fashion. For example, the meat can be transported in an open trough or along a transparent conveyor where the spacing of adjacent meat products and/or flow rate of the meat is controlled such that only a thin layer of meat product passes past the camera at any one time. In this aspect, the light source can be placed adjacent to a transparent floor of the trough or conveyor that is open at the top.

In another aspect, the thickness of the process stream is positively constrained while performing the optical inspection. Such positive control of the stream thickness during the optical inspection can be achieved by utilizing an inspection fixture 700 inserted in a flow path. Fixture 700 (see FIG. 15) includes a pair of opposed transparent walls 710, 720 or windows forming the upper and lower portions of a rectangular flow channel. The light assembly 650 can be mounted to one of the walls 710, and meat passing through the channel between the walls 710, 720 is optically inspected with a camera on the opposite side of the opposing transparent wall 720. The spacing T between the inside surfaces of the transparent walls 710, 720 windows provides a limit to the thickness of the meat product in the fixture. This spaced plate configuration is effective when the process stream is conveyed as a fluid, such as by pumping a slurry of whole meat products. The inspection fixture can also be used when pumping or otherwise conveying ground product through a process line. For a given intensity and configuration of the light source 650, it may be desirable to have a thinner process stream for ground product than for a slurry of whole meat due to the increased density of the ground product.

Increased reliability of detection can achieved by providing multiple optical inspection stations in series along the process stream. In one useful aspect, the multiple optical inspection stations have the light sources and detection equipment on reversed sides of the process stream such that optical backlighting occurs from one side (the bottom) of the process steam in the first station and from the other side (the top) at the next station. Reversing the inspection orientation reverses the depth of the bones relative to the respective camera, which can improve the overall detection capabilities.

Figure 16:
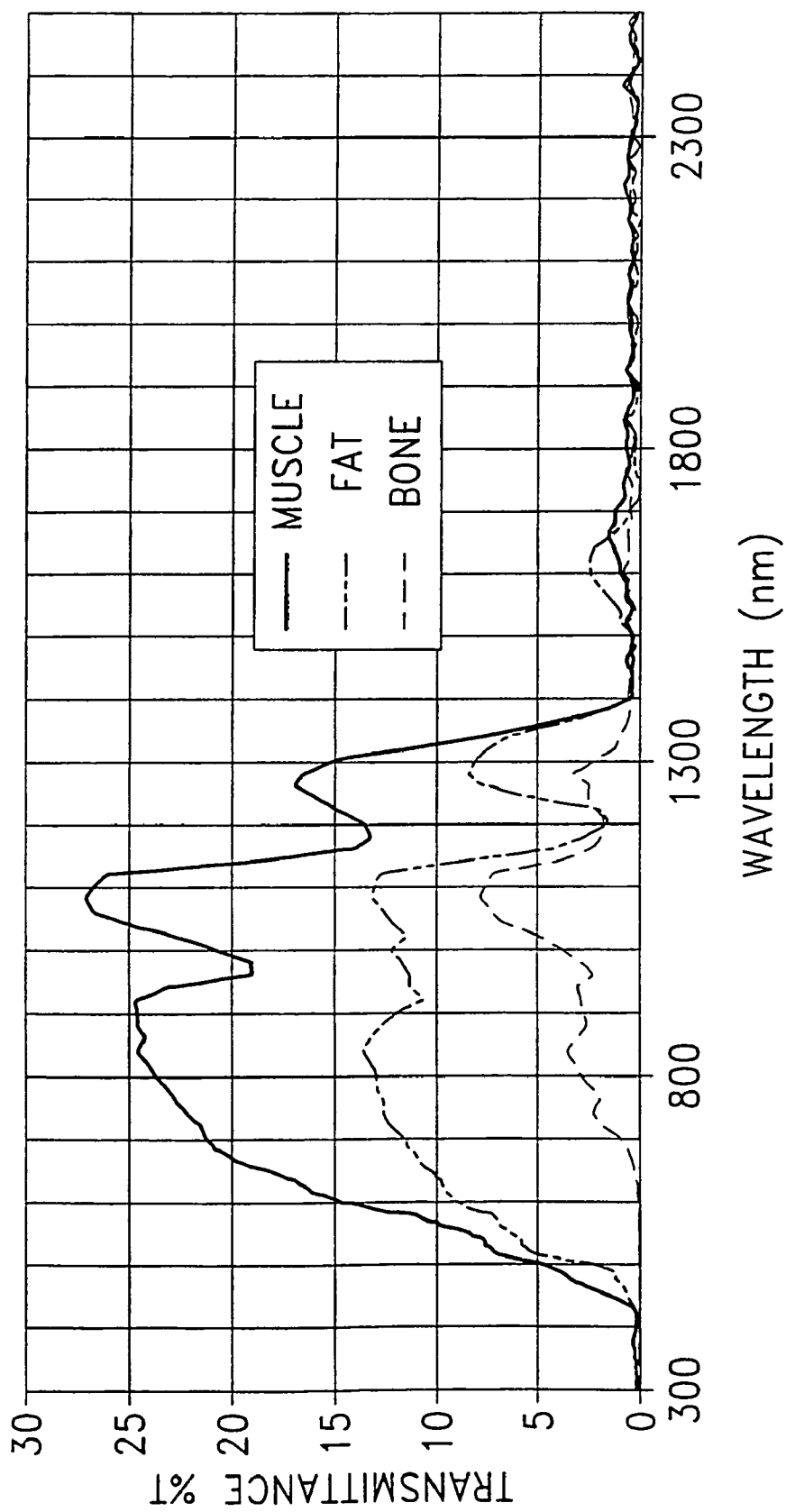
FIG. 16 is an exemplary plot of percent transmittance versus optical wavelength for the muscle, fat, and bone of chicken breasts.

When performing optical inspection according to aspects of the present invention, the wavelength of the substantially monochromatic light source is selected to provide a high degree of contrast between the desirable product (the chicken meat or fat) and the undesirable foreign material (the bone). A useful procedure for selecting the appropriate wavelength is to obtain optical transmittance curves across a range of wavelengths for both the desirable product and the undesirable foreign material and to select a wavelength where there is substantial difference in transmittance between the desirable and undesirable product as indicated by the transmittance curves. In one aspect, the wavelength is selected such that the undesirable product (the bone) is substantially opaque to the selected wavelength, i.e. the optical transmittance is close to zero under measurement conditions. In the illustrated embodiment, green light has been found to be surprisingly effective. An exemplary plot of the percent transmittance for various wavelengths of light through 0.25 inches of the muscle, fat, and bone from chicken breasts is shown in FIG. 16. The FIG. 16 transmittance curves demonstrate various degrees of optical transmittance for the various materials. In particular, the chicken bone is substantially opaque to light below about 600 nm whereas in this lower portion of the spectrum, the chicken fat and muscle does not become opaque until the wavelength drops below about 420 nm.

Figure 11:
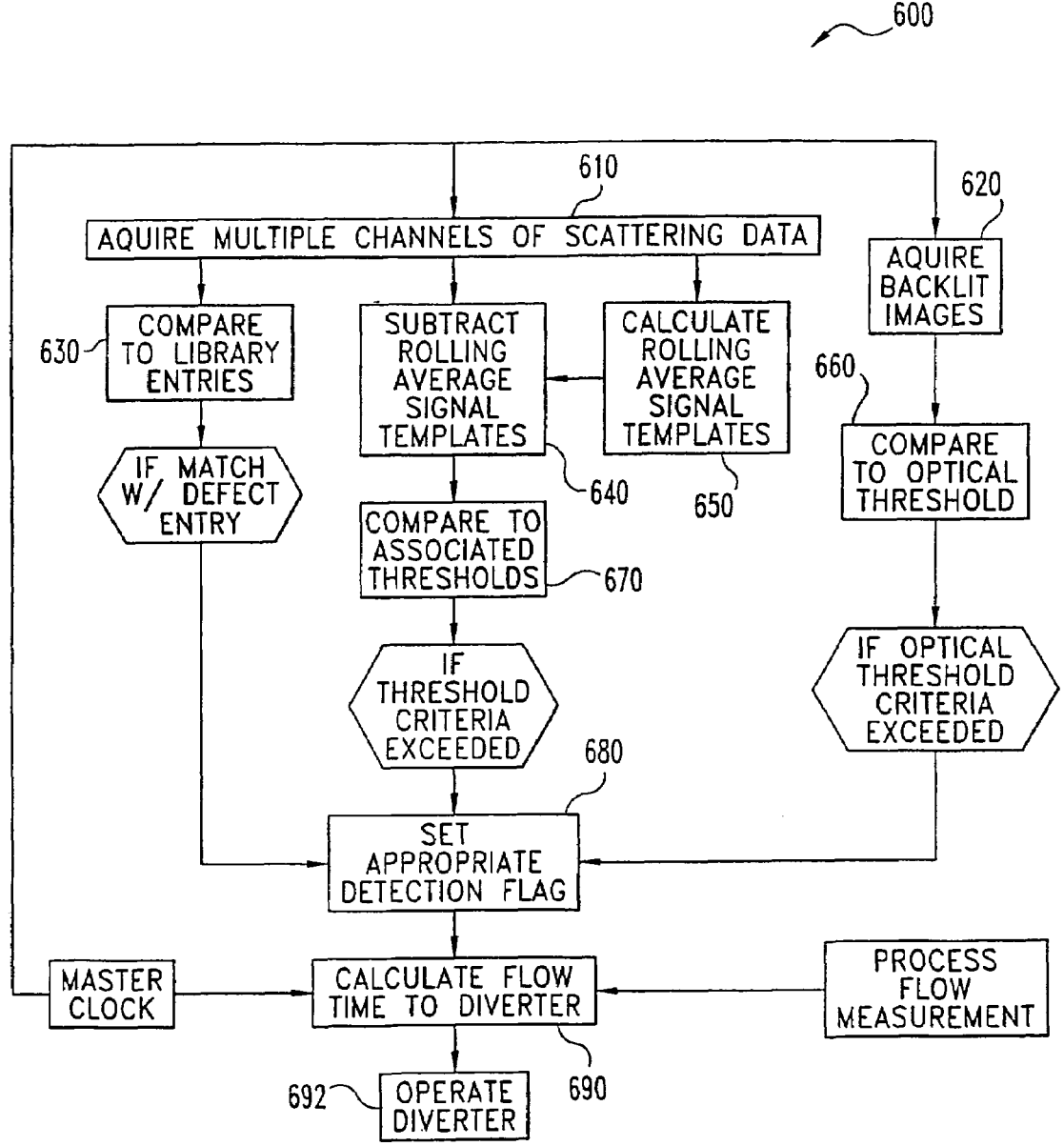
FIG. 11 is a flow chart of one embodiment of a process for detecting foreign material.

Turning now to FIG. 11, a flow chart of a combined ultrasound scattering-optical backlighting detection technique useful for determining the presence of foreign material in a process stream is illustrated. Process 600 begins with the acquisition of multiple channels of ultrasound scattering data in action 610. The multiple channels of data correspond to ultrasound receivers at fixed spatial locations along the process flow path and can be acquired by any of the systems and techniques described herein.

A rolling average of the signal templates for each channel of data is then calculated in action 650. The rolling average is representative of scattering from the bulk material in the process stream and is subtracted from the acquired scattering data in action 640, with the resulting signals compared to associated thresholds in action 670. If a threshold criteria is met, an appropriate detection flag is set in action 680. As described above, the threshold criteria can be one or more receivers trained on overlapping process flow volumes exceeding associated thresholds. Accordingly, the particular detection flag that is set will depend on the spatial location of the receiver or receivers which triggered the flag. In action 690 information regarding the process flow rate and the overall time are used to calculate an appropriate delay, and a diversion valve is operated in action 692 to remove the foreign material from the process stream.

The scattering data are also compared to a library of entries in action 630. The library contains entries corresponding to scattering signals from known occurrences of foreign material in the process stream. Upon finding a substantial match, for example with a trained neural network, a detection flag is set in action 680, a delay is calculated in action 690, and the diversion valve is operated in action 692.

Concurrently with the acquisition of scattering data in action 610, backlit images of the process stream are acquired in action 620. These backlit images are acquired by any of the system or techniques described herein or by any means know in the art. Most preferably, the backlit images include light in a wavelength range that achieves a high degree of contrast in the flow stream, which for detecting bone in chicken meat is between about 500-600 nm. The images are captured as single frames and digitized for comparison of one or more portions of the image to associated thresholds. If the threshold criteria is met, an appropriate detection flag is set in action 680. The optical detection flag reflects not only the spatial location of the optical inspection station, but also the spatial location within a captured image (e.g. the coordinates), recognizing that a single image can include a large area of the process stream. The flow time for the optically detected foreign material is calculated in step 690, and the diversion valve is operated in action 692.

In one variation of the technique, the optically backlit images are captured at a rate sufficient to permit a single defect to be visible in several of the captured images, for example at least 3 or more of the captured images, before the defect will have traveled completely through the view field. Where the view field of the captured images has a length L perpendicular to the flow direction and the process stream passes through the view field at a constant velocity of V, the images are preferable captured at a rate greater than 3 times V/L and more preferably greater than about 5 times V/L. In this variation, by monitoring the coordinates of detected defects, the location of a defect can be tracked as it passes through the view field based on the location of the defect in a prior captured image, the flow rate of the process stream, and the interval between captured images. Optionally, the relative location of defects is tracked through a series of captured images and the optical detection flag is set only if a particular suspected defected is detected in more than one of the captured images. Requiring redundancy prior to setting a detection flag is a mechanism for increasing the reliability of the optical detection methodology.

When utilizing complementary detection methodologies, for example ultrasound and optical backlighting, conflicts can arise when foreign material (bone) is detected by one technique but not by the other. In one variation of the combination technique, foreign material detected by the optical backlighting are conclusively determined to be defects and the relevant product is rejected or diverted whether or not the ultrasound technique also detected the same foreign material. If the ultrasound detects a potential defect but the optical backlighting does not, resolution of whether to conclude foreign material is present is a function of the depth of the possible foreign material as determined by the ultrasound scattering response. The depth of the possible defect, for purposes of the present analysis, is calculated from the time delay between the interrogation pulse and the received signal indicating a potential defect. Ultrasound detected foreign material that is deep in the process stream (i.e. further away from the camera) can be given more reliability weight than foreign material detected by the ultrasound at the surface (i.e. nearer the camera) in recognition of the increased relative reliability of the ultrasound technique in detecting buried bones.

In another variation of the technique, the rolling average of the ultrasound signals calculated in step 650 excludes any signals determined to represent foreign material. This can be accomplished by calculating the rolling average with signals that do not meet threshold criteria. In another variation, signals that are found to meet threshold criteria are added to the library to thereby expand the library under operating conditions.

As describe above, it is not necessary to perform the optical inspection techniques described herein in combination with the ultrasound inspection techniques described herein, as each can be employed single as well as in combination with other complimentary methodologies as would occur to those of skill in the art.

Figure 19:
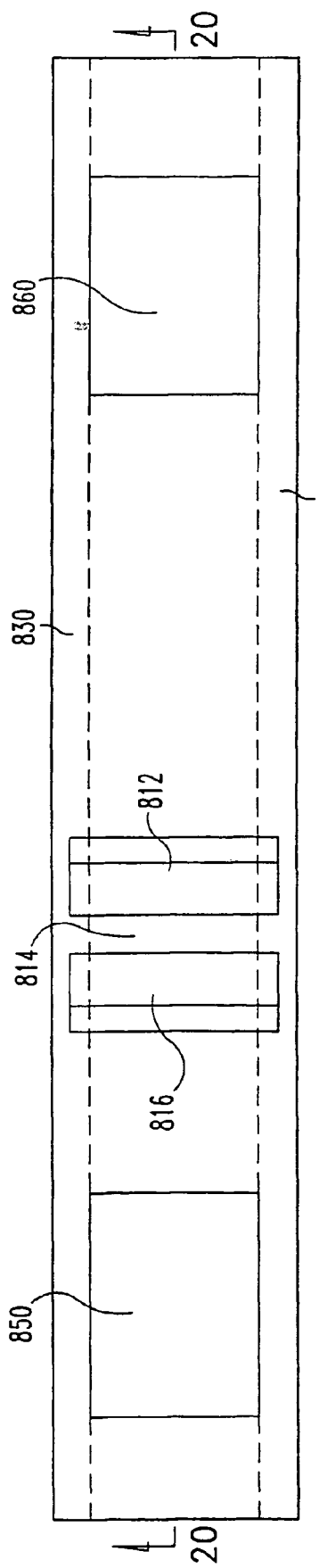
FIG. 19 is a top view of a flow channel having transparent windows and transducer mounting locations for performing optical backlighting inspection and ultrasonic inspection of a process stream according to embodiments of the present invention.
Figure 20:
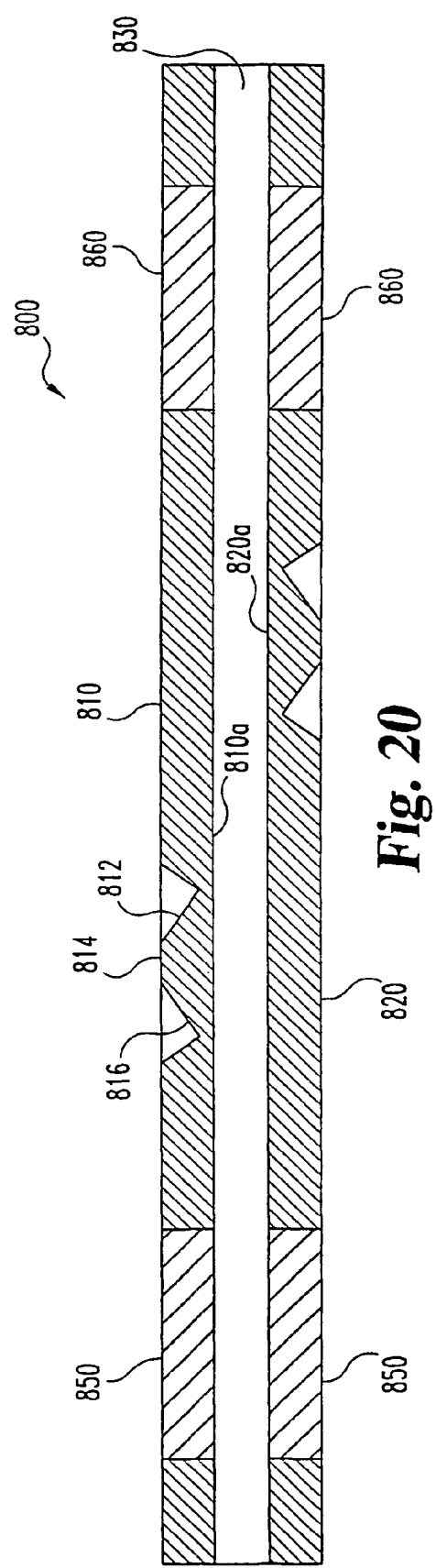
FIG. 20 is a side sectional view of the FIG. 19 flow channel.

Turning now to FIGS. 19 and 20, a flow conduit 800 for performing optical inspection and ultrasonic interrogation in series along a single flow path is depicted. Conduit 800 is formed by opposed upper an lower walls 810, 820 and an opposed pair of sidewalls 830, 840. The inside surfaces 810a, 820a of the upper and lower walls, as well as the inside side surfaces of the sidewalls, are generally flat and define a flow path with a generally rectangular cross section. Windows 850, 860 are provided in each of the upper and lower walls 810, 820 at the ends of the conduit 800. The windows 850, 860 in each of the walls 810, 820 are aligned on opposite sides of the flow path to provide two locations for optical inspection of the material the conduit 800 according to the techniques described herein. The provision of two sets of windows 850, 860 provides to opportunity to perform optical backlighting from both sides of the flow path. The upper and lower walls 810, 820 can be constructed as a solid piece of machined polysulphone with polycarbonate pieces glued in place to form the windows 850, 860.

Between the windows 850, 860, the upper wall 810 is machined to provide a set of surfaces 812, 814, 816 that serve as ultrasound transducer mounting locations for performing ultrasonic inspection according to the techniques described herein. Corresponding surfaces for ultrasound transducers are provided in the lower wall 820 to provide the option for complementary ultrasound inspection from the bottom side of the flow path. The ultrasound mounting surfaces in the lower wall 820 are downstream from the surfaces 812, 814, 816 in the upper wall 810 to minimize interference between the two locations. A conventional flow meter (not shown), such as a commercially available ultrasonic flow meter, is mounted along the flow path 800.

Figure 21:
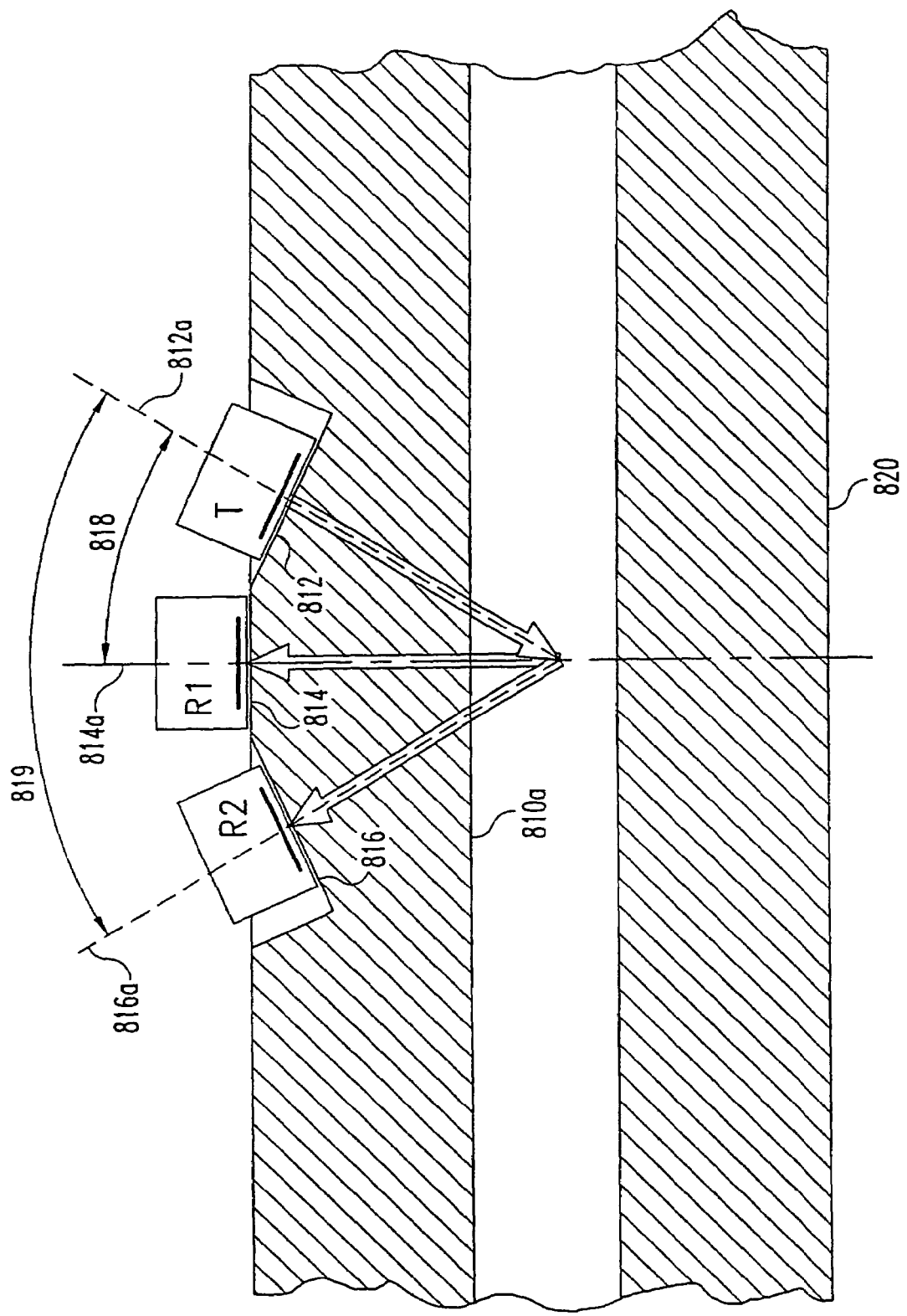
FIG. 21 is an enlarged side sectional view of ultrasound transducers mounted on the FIG. 19 flow channel illustrating multiple receivers arranged at different angles to a common interrogation axis.

Turning now to FIG. 21, surfaces 812, 814, 816 are non parallel to each other and receive a set of ultrasound transducers, T, R1 and R2. The transmitter T is aligned along an interrogation axis 812a, and the receivers R1 and R2 are aligned along detection axes 814a and 816a. The angle 819 between the interrogation axis 812a and the detection axis 816a is approximately twice the angle 818 between axis 812a and axis 814a. In one aspect angle 819 is at least about 1.5 times angle 818. A suitable value for angle 818 with unfocused transducers T, R1, R2 is about 31 degrees. As depicted, axis 814*a* is approximately perpendicular to the bulk flow direction of the conduit, which bulk flow direction can be either to the left or right as shown in FIG. 21. In other aspects, axis 814*a* is not-perpendicular with the bulk flow direction.

Use of multiple receivers R1, R2 at substantially different angles to a common interrogation axis 812*a* provides a mechanism to detect high aspect ratio objects at different orientations. It has been found that off angle ultrasound scattering at lower angles (from T to R1) is preferentially sensitive to spherical targets or elongated targets with their long axis perpendicular to the bulk flow direction. Scattering at higher angles (from T to R2) is preferentially sensitive to scattering from targets with their long axis parallel to the bulk flow direction.

Figure 22:
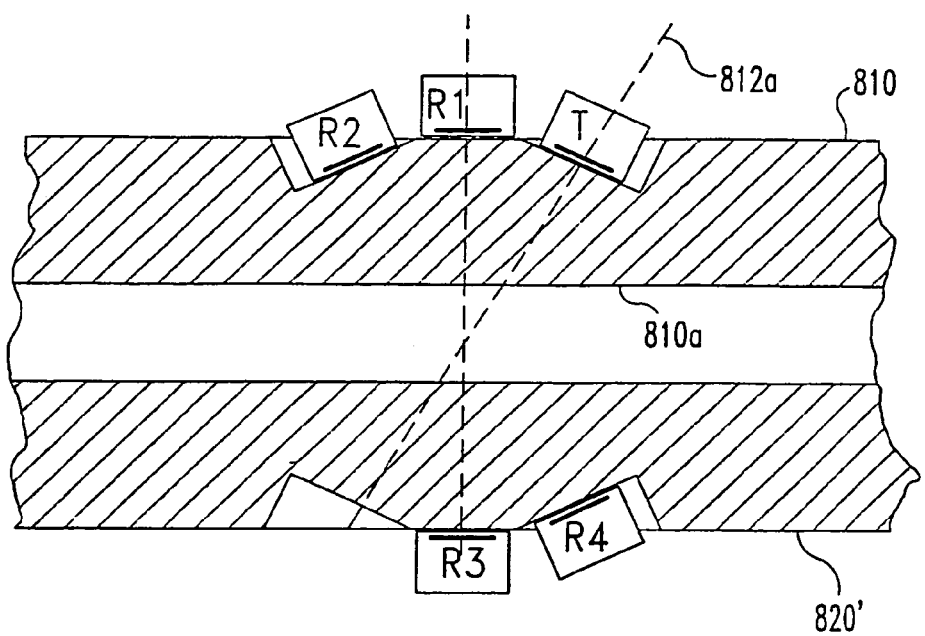
FIG. 22 is an enlarged side sectional view of an alternative configuration for the FIG. 19 flow channel wherein ultrasonic receivers are provided in both the upper and lower walls of the channel.
Figure 23:
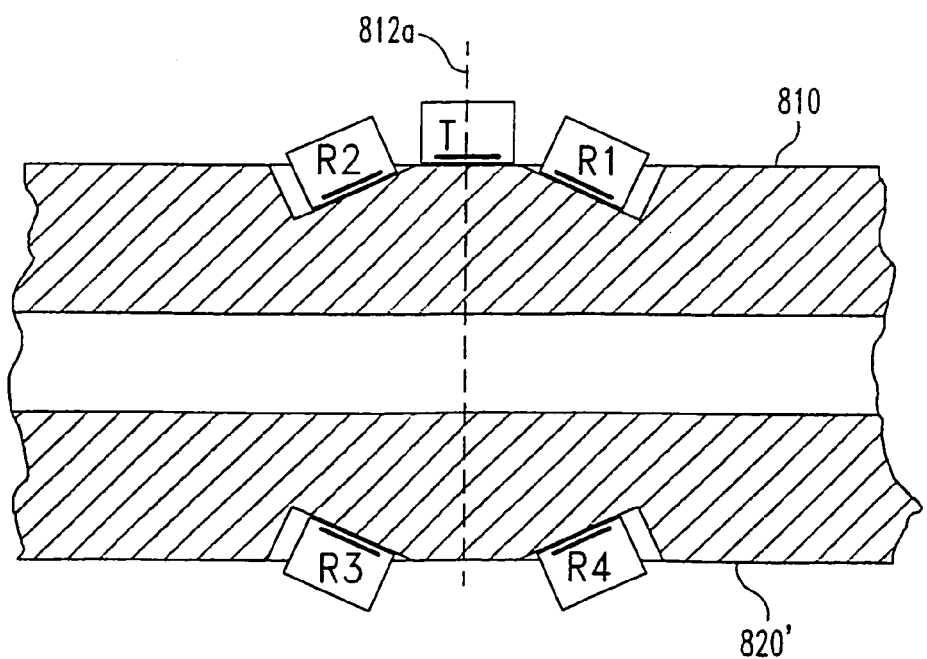
FIG. 23 is an enlarged side sectional view of an ultrasound transducer configuration for the FIG. 22 flow channel.

Turning now to FIGS. 22 and 23, variations on the transducer configurations for the FIG. 19 flow channel are depicted wherein receivers R1 and R2 are acoustically associated with the upper wall 810 and receivers R3 and R4 are acoustically associated with the lower wall 820' which is spaced from the upper wall 810 to form at least a portion of the flow path. Each of the receivers R1-R4 receive the off angle scattering from transmitter T mounted on the upper wall 810. The receivers R3 and R4 are coupled to mounting surfaces in the lower walls, where those mounting surfaces can be a mirror images of the mounting surfaces 812, 814, 816 provided in the upper wall 810.

In the FIG. 22 variation, transmitter T and receivers R1 and R2 are mounted in the top wall 810 as described above with respect to FIG. 19, with receivers R1 and R2 aligned at different angles to the interrogation axis 812*a* defined by transmitter T. Receivers R3 and R4 are mounted in the bottom wall and are likewise aligned at different angles to the interrogation axis 812*a*, for example about 150 and 120 degrees respectively.

In the FIG. 23 variation, transmitter T is positioned between receivers R1 and R2 in the top wall 810 such that receivers R1 and R2 are arranged at approximately equivalent angles to the interrogation axis 812*a* with one receiver angled upstream (for example R1) and the other angled downstream (for example R2). The interrogation axis 81*a* can be approximately perpendicular to the flow direction. Receivers R3 and R4 are mounted in the lower wall 820' and are also positioned at generally equivalent angles with respect to the interrogation axis 812*a*.

As described above, the exact angles between receiver axes and an interrogation axis will vary in different embodiments and for different applications of the present invention. However, it is to be understood that, in the embodiments depicted in FIGS. 22 and 23, the receivers R3, R4 in the lower wall 820' will typically receive ultrasound scattered at angles greater than 90 degrees from the interrogation axis 812*a* of transmitter T mounted in the upper wall 810, whereas the receivers R1, R2 in the upper wall 810 will typically receive ultrasound scattered at angles less than 90 degrees.

Figure 27:
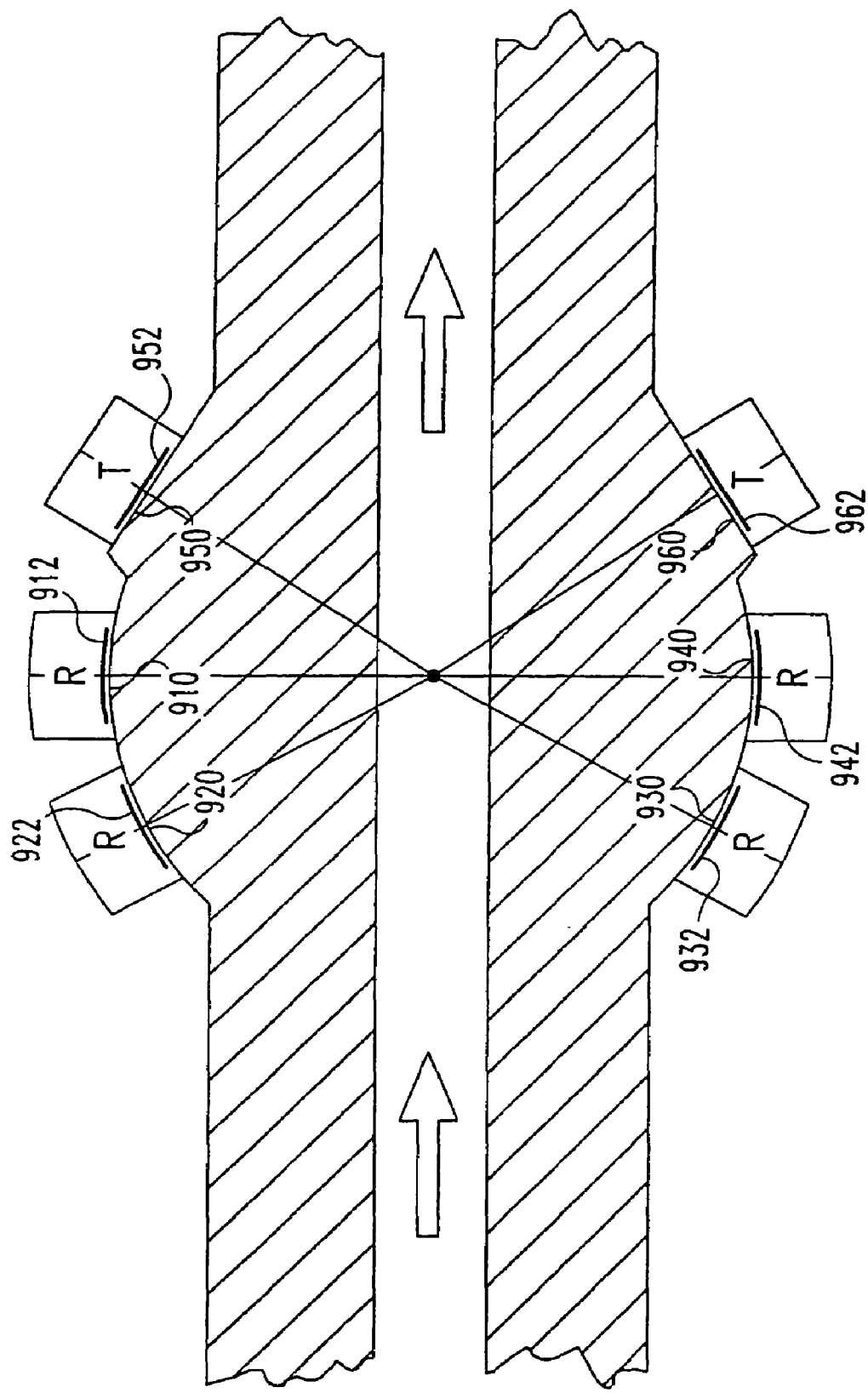
FIG. 27 is an enlarged side sectional view of an ultrasound transducer configuration for an alternative to the FIG. 22 flow channel where the mounting surfaces for the receivers are curved and the mounting surface for the transmitters are flat.

Turning now to FIG. 27 a further variation is depicted wherein the non-parallel mounting surfaces for receiving the ultrasound transducers are a mixture of curved and flat surfaces. The curved mounting surfaces 910, 920, 930, 940 are shaped to match the face of correspondingly curved transducers elements 912, 922, 932, 942 respectively, for example the cylindrically curved piezo-ceramic transducer element of a cylindrically focused transducer or a spherically curved surface of a spherically focused transducer. The flat mounting surfaces 950, 960 are shaped to match the face of flat transducer element 952, 962. As described above, when operating as a transmitter, a flat transducer element generally produces an unfocused flat beam, and as illustrated in FIG. 27, the flat transducers operate as transmitters and the curved transducers operate as receivers of off angle scattering. However, in other forms each of the mounting surfaces can receive an ultrasound transducer for operation as a transmitter, a receiver, or as both.

For the curved mounting surfaces 910, 920, 930, 940, the radius of curvature is physically measured from the transducer face to be matched. The selection of the curvature of the respective face of the transducer element depends on the desired characteristics for the transducer based on the given geometry and material characteristics. For example, the radius of curvature can be selected to locate the focal point (or line) for a particular transducer at a particular location within the flow channel, for example at the centerline. As illustrated all transducers are aligned along axes that intersect at a single point, though the particular orientation of each transducer and the focal characteristics can be the same or different for the different transducers. Accordingly, the radius of curvature can be the same or different for each of the elements 912, 922, 932, 942. Nearly identical surface curvature, or lack thereof, between the mounting surfaces and the transducer elements in FIG. 27 can reduce the need for intervening delay material or acoustic couplant between the face of the transducer element and the mounting surface in which case the elements can be in direct or nearly direct contact with the corresponding mounting surfaces.

Figure 25:
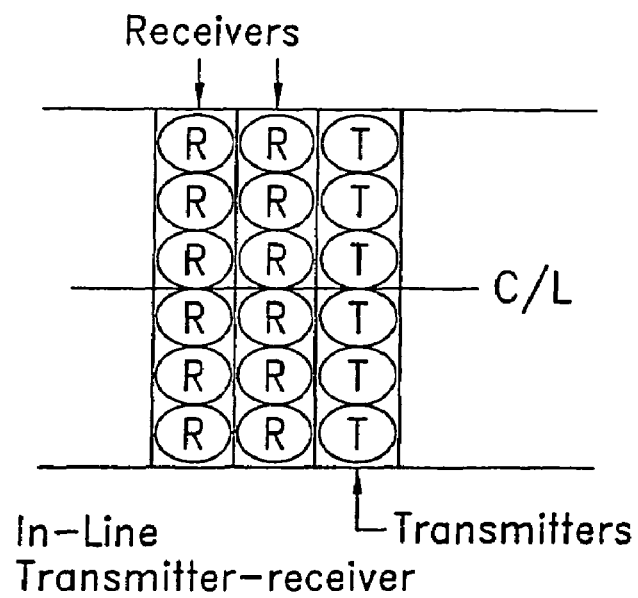
FIG. 25 is a top plan view of inline transmitters and receivers useful in, for example, the FIG. 21 embodiment with C/L indicating the centerline of the flow channel.
Figure 26:
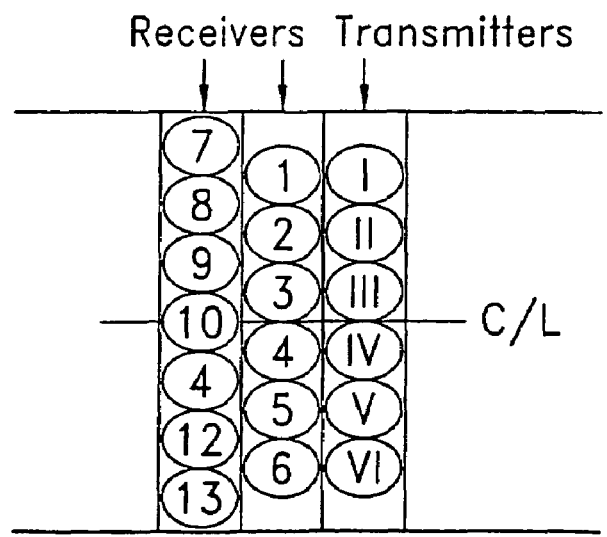
FIG. 26 is a variation of the FIG. 25 top plan view illustrating staggered receivers.

Various configurations for the transmitters and receivers are contemplated. An exemplary top plan views of a set of inline transmitters and receivers is depicted in FIG. 25, with C/L indicating the centerline of the flow channel parallel to the flow direction. It is understood that inline transmitters and receivers indicates that a pair of receivers R are in a single line with a transmitter T. The depicted transmitters T and receivers R can be mounted on corresponding mounting surfaces as described above with respect to FIGS. 21 and 27, for example. FIG. 26 illustrates a variation on the inline orientation of FIG. 25 wherein the receivers are staggered.

EXAMPLES

Example 1

The inspection station depicted in FIGS. 8A and 8B are used to detect bones in chicken breast, where water is used in place of wedge 446 to couple sound into and out of the channel. A packed chicken breast slurry is contained in a channel six inches wide and ¾ inch high and traveling at a speed up to about 15 inches/second. Eight cylindrically focused ultrasound receivers are positioned around a pair of central longitudinally extending and cylindrically focused transmitters where the relative angle between transmitter axis and receiver axis is between about 18 and 22 degrees. The focal depth of all transducers is 2 inches and the transmitter operates at a 1 MHz inspection frequency. Threshold amplitude detection and the requirement for more than one receiver to exceed the threshold is used to detect chicken bones of various types and sizes. In a variation, the transmitters and receivers are spherically focused.

Example 2

The inspection station depicted in FIG. 21 was used to detect bones in chicken breast. Eight ultrasound receivers were positioned around a pair of transmitters where the relative angle between transmitter axis and receiver axis was between 18 and 22 degrees. The transmitter operated at a 1 MHz inspection frequency. A packed chicken breast slurry was contained in a polysulfone channel six inches wide and one inch high. The chicken breast slurry was inspected both while stationary and while traveling at a speed of about 8 inches/second. Using threshold amplitude detection over 85% of manually inserted chicken bones of various types and sizes were detected.

Example 3

Figure 17:
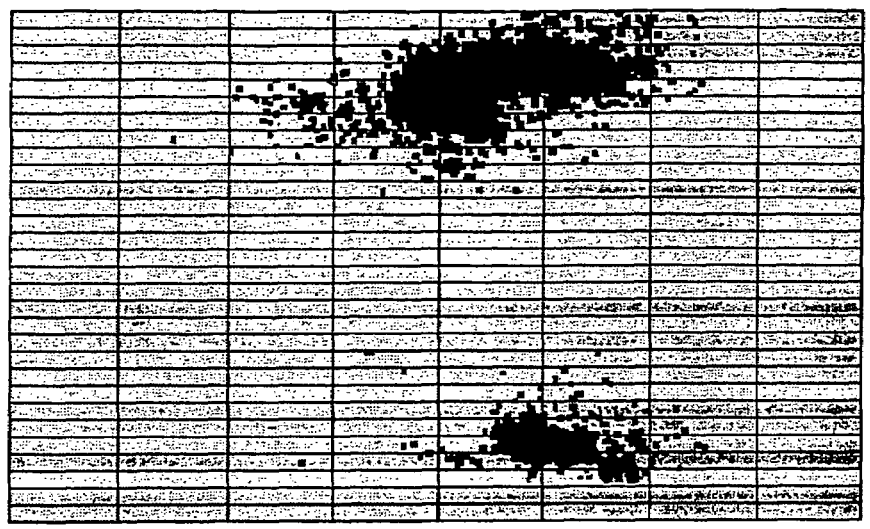
FIG. 17 is an exemplary gray scale captured image of a chicken breast slurry with grid lines indicating image processing units.
Figure 18:
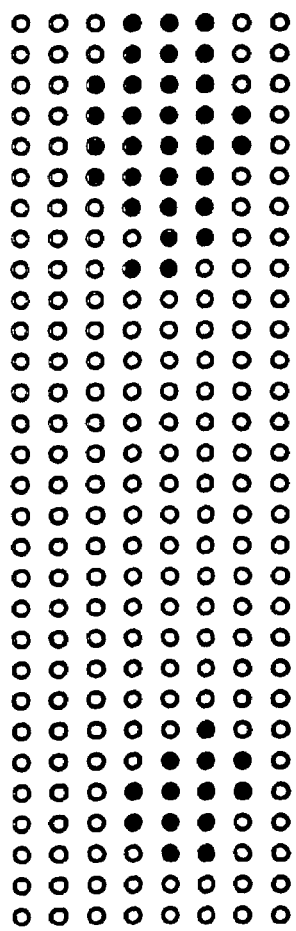
FIG. 18 is an exemplary representation of the image processing units of FIG. 17 processed to determine the presence of bone in each unit, where a darkened circle represents detected bone in the respective unit.

The inspection station depicted in FIG. 15 was used to detect bones in chicken breasts. A packed chicken breast slurry was contained in a channel six inches wide and 1 inch high and traveled at a speed of 15 inches/second. Two inspection systems were employed, one for the top surface and one for the bottom. An exemplary gray scale image from the top camera is shown in FIG. 17, with the flow of chicken breasts being from bottom to top of the image. For processing, the pixel data was reduced to eight equally spaced zones across for each line of a camera frame, and every other line of the 60 line image was discarded for efficiency, resulting in the 30×8 grid shown superimposed on the image in FIG. 17. The image data in each grid block was processed by comparing against a high and low threshold. FIG. 18 is a graphical representation of the thresholded image data for each image block of the grid, where a dark circle represents bone detected in the respective image location.

While the invention has been illustrated and described in detail in the drawings and foregoing description, the same is to be considered as illustrative and not restrictive in character, it being understood that only preferred embodiments have been shown and described and that all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. All publications, patents, and patent applications cited in this specification are herein incorporated by reference as if each individual publication, patent, or patent application were specifically and individually indicated to be incorporated by reference and set forth in its entirety herein. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary.

What is claimed is:

1. A system for detecting foreign material in meat comprising:
    a planar array of LEDs producing source light having a wavelength less than about 600 nm operably associated with a wall substantially transparent to the source light and defining a portion of a meat conveyor optically backlit by the array of LEDs;
    a camera operable to capture source light passing through meat transported by the conveyor;
    a processing device operable to capture images of the meat from the camera and to determine the presence and spatial location of foreign material in the meat when at least a portion of the captured image exceeds a predetermined threshold;
    one or more inspection devices operable to transmit ultrasound to interrogate the meat;
    a plurality of spaced receivers each operable to receive an off-angle ultrasound scattering response to interrogation with the ultrasound; and
    a processing device operable to determine presence of a foreign material in the process stream based on a comparison of the off-angle ultrasound scattering response to a predetermined threshold.

2. The system of claim 1 wherein the plurality of receivers include first and second receivers aligned along first and second detection axes respectively and wherein the detection axes each form substantially different angles with an interrogation axis of one of the one or more inspection devices.

3. The system of claim 2 wherein the substantially different angles are in a ratio of at least about 1.5 to 1.

4. A system for determining the presence of foreign material in a process stream comprising:
    a conduit for conveying a process stream, the conduit defined by at least one wall having an inside flat surface and at least three surfaces non-parallel to each other in acoustic communication with the inside flat surface;
    at least one ultrasound interrogation device on one of the three non-parallel surfaces and operable to transmit ultrasound through the inside flat surface to interrogate the process stream;
    a plurality of spaced receivers on other ones of the three non-parallel surfaces and each operable to receive an off-angle ultrasound scattering response to interrogation with the ultrasound for determining presence of a foreign material in the process stream; and
    a light source producing source light in the range of 500 to 600 nm for performing optical backlighting of the process stream through at least one window portion of the conduit substantially transparent to the source light.

5. The system of claim 4 wherein the plurality of receivers include first and second receivers aligned along first and second detection axes respectively and wherein the detection axes each form substantially different angles with an interrogation axis of one of the one or more inspection devices.

6. The system of claim 4 wherein the light source includes a planar array of LEDs.

7. The system of claim 4 further comprising:
    a camera for capturing optically backlit images of the process stream; and
    a processing device operable to capture images of the process stream from the camera and to determine presence of foreign material when at least a portion of the captured image exceeds a predetermined threshold and further operable to determine presence of foreign material in the process stream based on a comparison of the off-angle ultrasound scattering response to a predetermined threshold.

8. A system comprising:
    a conduit having a pair of opposed flat walls operable to receive a process stream,
    one or more inspection devices operable to transmit ultrasound through at least one of the flat walls to interrogate the process stream,
    a plurality of spaced receivers each operable to receive through at least one of the flat walls an off-angle ultrasound scattering response to interrogation with the ultrasound; and a processing device operable to determine presence of a foreign material in the process stream based on a comparison of the off angle ultrasound scattering response to a predetermined threshold.

9. The system of claim 8 wherein at least two receivers and an inspection device are on the same side of one of the opposed flat walls and the receivers are trained on overlapping volumes and are aligned at substantially different angles to a common interrogation axis.

10. The system of claim 9 wherein the at least two receivers are cylindrically focused and the inspection device produces a substantially flat ultrasonic beam.

11. The system of claim 8 wherein the conduit defines a bulk flow direction for the process stream between the opposed flat walls and the walls are separated by a distance less than the dimension of the walls transverse to the bulk flow direction.

12. The system of claim 11 wherein the plurality of receivers include at least two receivers trained on non-overlapping volumes and the processing device is operable to provide an indication of the spatial location of the foreign material in the process stream.

* * * * *